US010526353B2

(12) United States Patent
Silvestrini

(10) Patent No.: US 10,526,353 B2
(45) Date of Patent: Jan. 7, 2020

(54) LENS OIL HAVING A NARROW MOLECULAR WEIGHT DISTRIBUTION FOR INTRAOCULAR LENS DEVICES

(71) Applicant: LensGen, Inc., Irvine, CA (US)

(72) Inventor: Thomas Silvestrini, Alamo, CA (US)

(73) Assignee: LensGen, Inc., Irvine, CA (US)

( * ) Notice: Subject to any disclaimer, the term of this patent is extended or adjusted under 35 U.S.C. 154(b) by 0 days.

(21) Appl. No.: 15/607,305

(22) Filed: May 26, 2017

(65) Prior Publication Data

US 2017/0342096 A1    Nov. 30, 2017

Related U.S. Application Data

(60) Provisional application No. 62/342,590, filed on May 27, 2016.

(51) Int. Cl.
| | |
|---|---|
| *A61F 2/16* | (2006.01) |
| *C07F 7/08* | (2006.01) |
| *C08G 77/14* | (2006.01) |
| *C08G 77/24* | (2006.01) |
| *C09D 183/04* | (2006.01) |

(Continued)

(52) U.S. Cl.
CPC .............. *C07F 7/0838* (2013.01); *A61F 2/16* (2013.01); *A61F 2/1635* (2013.01); *C08G 77/04* (2013.01); *C08G 77/14* (2013.01); *C08G 77/24* (2013.01); *C08L 83/08* (2013.01); *C09D 183/04* (2013.01); *C10M 107/50* (2013.01); *C10M 171/04* (2013.01); *C08L 83/12* (2013.01); *C10M 2229/0415* (2013.01); *C10M 2229/0425* (2013.01); *C10N 2220/021* (2013.01); *C10N 2220/022* (2013.01); *C10N 2230/36* (2013.01); *C10N 2240/66* (2013.01); *C10N 2270/00* (2013.01)

(58) Field of Classification Search
None
See application file for complete search history.

(56) References Cited

U.S. PATENT DOCUMENTS

| 4,032,502 | A | | 6/1977 | Lee et al. |
| 4,373,218 | A | * | 2/1983 | Schachar .............. A61F 2/1613 349/13 |

(Continued)

FOREIGN PATENT DOCUMENTS

| EP | 0356050 A1 | 2/1990 |
| EP | 0766540 B1 | 8/1999 |

(Continued)

OTHER PUBLICATIONS

Gallagher-Wetmore et al., "Supercritical fluid processing: a new dry technique for photoresist developing", 1995, 16 pages. (Year: 1995).*

(Continued)

*Primary Examiner* — Robert S Loewe
(74) *Attorney, Agent, or Firm* — Knobbe, Martens, Olson & Bear LLP

(57) ABSTRACT

A silicone oil having a mean molecular weight average greater than about 20,000 Daltons, with no more than about 3% to about 4% of the total silicone oil by weight being comprised of components having a molecular weight less than about 15,000 Daltons. In some embodiments, the silicone oil is used in intraocular lens devices.

20 Claims, 5 Drawing Sheets

(51) Int. Cl.
*C10M 107/50* (2006.01)
*C10M 171/04* (2006.01)
*C08G 77/04* (2006.01)
*C08L 83/08* (2006.01)
*C08L 83/12* (2006.01)

(56) References Cited

U.S. PATENT DOCUMENTS

| | | | |
|---|---|---|---|
| 4,512,040 A | 4/1985 | McClure | |
| 4,585,457 A | 4/1986 | Kalb | |
| 4,720,286 A | 1/1988 | Bailey et al. | |
| 4,731,078 A | 3/1988 | Stoy et al. | |
| 4,822,360 A | 4/1989 | Deacon | |
| 4,842,601 A | 6/1989 | Smith | |
| 4,882,368 A | 11/1989 | Elias et al. | |
| 4,888,012 A | 12/1989 | Horn et al. | |
| 4,892,543 A | 1/1990 | Turley | |
| 4,932,966 A | 7/1990 | Christie et al. | |
| 5,035,710 A | 7/1991 | Nakada et al. | |
| 5,059,668 A | 10/1991 | Fukuda et al. | |
| 5,074,876 A | 12/1991 | Kelman | |
| 5,091,121 A | 2/1992 | Nakada et al. | |
| 5,152,788 A | 10/1992 | Isaacson et al. | |
| 5,167,883 A * | 12/1992 | Takemasa | B29C 71/00 264/28 |
| 5,171,773 A | 12/1992 | Chaffe et al. | |
| 5,227,447 A * | 7/1993 | Sato | C08G 77/08 528/12 |
| 5,236,970 A | 8/1993 | Christ et al. | |
| 5,264,522 A | 11/1993 | Mize et al. | |
| 5,275,623 A | 1/1994 | Sarfarazi | |
| 5,278,258 A | 1/1994 | Gerace et al. | |
| 5,312,860 A | 5/1994 | Mize et al. | |
| 5,336,487 A * | 8/1994 | Refojo | A61K 31/695 424/78.04 |
| 5,443,506 A | 8/1995 | Garabet | |
| 5,447,987 A | 9/1995 | Sato et al. | |
| 5,489,302 A | 2/1996 | Skottun | |
| 5,583,178 A | 12/1996 | Oxman et al. | |
| 5,607,472 A | 3/1997 | Thompson | |
| 5,665,794 A | 9/1997 | Maxson et al. | |
| 5,854,310 A | 12/1998 | Maxson | |
| 6,071,439 A * | 6/2000 | Bawa | B29C 37/0003 134/31 |
| 6,117,171 A | 9/2000 | Skottun | |
| 6,197,057 B1 | 3/2001 | Peyman et al. | |
| 6,361,561 B1 * | 3/2002 | Huo | A61L 27/18 523/113 |
| 6,551,354 B1 | 4/2003 | Ghazizadeh et al. | |
| 6,616,691 B1 | 9/2003 | Tran | |
| 6,695,881 B2 | 2/2004 | Peng et al. | |
| 6,730,123 B1 | 5/2004 | Klopotek | |
| 6,836,374 B2 | 12/2004 | Esch et al. | |
| 6,855,164 B2 | 2/2005 | Glazier | |
| 6,858,040 B2 | 2/2005 | Nguyen et al. | |
| 6,860,601 B2 | 3/2005 | Shadduck | |
| 6,926,736 B2 | 8/2005 | Peng et al. | |
| 6,930,838 B2 | 8/2005 | Schachar | |
| 6,935,743 B2 | 8/2005 | Shadduck | |
| 6,966,649 B2 | 11/2005 | Shadduck | |
| 6,969,403 B2 | 11/2005 | Peng et al. | |
| 7,041,134 B2 | 5/2006 | Nguyen et al. | |
| 7,063,723 B2 | 6/2006 | Ran | |
| 7,068,439 B2 | 6/2006 | Esch et al. | |
| 7,122,053 B2 | 10/2006 | Esch | |
| 7,150,760 B2 | 12/2006 | Zhang | |
| 7,217,288 B2 | 5/2007 | Esch et al. | |
| 7,220,279 B2 | 5/2007 | Nun | |
| 7,223,288 B2 | 5/2007 | Zhang et al. | |
| 7,226,478 B2 | 6/2007 | Ting et al. | |
| 7,229,475 B2 | 6/2007 | Glazier | |
| 7,238,201 B2 | 7/2007 | Portney et al. | |
| 7,247,168 B2 | 7/2007 | Esch et al. | |
| 7,261,737 B2 | 8/2007 | Esch et al. | |
| 7,264,351 B2 | 9/2007 | Shadduck | |
| 7,276,619 B2 * | 10/2007 | Kunzler | A61K 31/695 556/466 |
| 7,278,739 B2 | 10/2007 | Shadduck | |
| 7,316,713 B2 | 1/2008 | Zhang | |
| 7,416,562 B2 | 8/2008 | Gross | |
| 7,438,723 B2 | 10/2008 | Esch | |
| 7,452,377 B2 | 11/2008 | Watling et al. | |
| 7,453,646 B2 | 11/2008 | Lo | |
| 7,485,144 B2 | 2/2009 | Esch | |
| 7,591,849 B2 | 9/2009 | Richardson | |
| 7,637,947 B2 | 12/2009 | Smith et al. | |
| 7,662,179 B2 | 2/2010 | Sarfarazi | |
| 7,675,686 B2 | 3/2010 | Lo et al. | |
| 7,753,953 B1 | 7/2010 | Yee | |
| 7,776,088 B2 | 8/2010 | Shadduck | |
| 7,780,729 B2 | 8/2010 | Nguyen et al. | |
| 7,815,678 B2 | 10/2010 | Nun | |
| 7,842,087 B2 | 11/2010 | Nun | |
| 7,854,764 B2 | 12/2010 | Nun | |
| 7,857,850 B2 | 12/2010 | Mentak et al. | |
| 7,981,155 B2 | 7/2011 | Cumming | |
| 7,985,253 B2 | 7/2011 | Cumming | |
| 7,986,465 B1 | 7/2011 | Lo et al. | |
| 7,998,198 B2 | 8/2011 | Angelopoulos et al. | |
| 7,998,199 B2 | 8/2011 | Nun | |
| 8,012,204 B2 | 9/2011 | Weinschenk, III et al. | |
| 8,018,658 B2 | 9/2011 | Lo | |
| 8,034,106 B2 | 10/2011 | Mentak et al. | |
| 8,034,107 B2 | 10/2011 | Stenger | |
| 8,038,711 B2 | 10/2011 | Clarke | |
| 8,048,155 B2 | 11/2011 | Shadduck | |
| 8,052,752 B2 | 11/2011 | Woods et al. | |
| 8,062,361 B2 | 11/2011 | Nguyen et al. | |
| 8,070,806 B2 | 12/2011 | Khoury | |
| 8,158,712 B2 | 4/2012 | Your | |
| 8,182,531 B2 | 5/2012 | Hermans et al. | |
| 8,187,325 B2 | 5/2012 | Zadno-Azizi et al. | |
| 8,197,541 B2 | 6/2012 | Schedler | |
| 8,216,306 B2 | 7/2012 | Coroneo | |
| 8,246,679 B2 | 8/2012 | Nguyen et al. | |
| 8,254,034 B1 | 8/2012 | Shields et al. | |
| 8,257,827 B1 | 9/2012 | Shi et al. | |
| 8,273,123 B2 | 9/2012 | Nun | |
| 8,303,656 B2 | 11/2012 | Shadduck | |
| 8,314,927 B2 | 11/2012 | Choi et al. | |
| 8,320,049 B2 | 11/2012 | Huang et al. | |
| 8,328,869 B2 | 12/2012 | Smiley et al. | |
| 8,361,145 B2 | 1/2013 | Scholl et al. | |
| 8,377,124 B2 | 2/2013 | Hong et al. | |
| 8,398,709 B2 | 3/2013 | Nun | |
| 8,414,646 B2 | 4/2013 | De Juan, Jr. et al. | |
| 8,425,597 B2 | 4/2013 | Glick et al. | |
| 8,425,599 B2 | 4/2013 | Shadduck | |
| 8,430,928 B2 | 4/2013 | Liao | |
| 8,447,086 B2 | 5/2013 | Hildebrand et al. | |
| 8,454,688 B2 | 6/2013 | Esch et al. | |
| 8,475,529 B2 | 7/2013 | Clarke | |
| 8,496,701 B2 | 7/2013 | Hermans et al. | |
| 8,500,806 B1 | 8/2013 | Phillips | |
| 8,545,556 B2 | 10/2013 | Woods et al. | |
| 8,579,972 B2 | 11/2013 | Rombach | |
| 8,585,758 B2 | 11/2013 | Woods | |
| 8,608,799 B2 | 12/2013 | Blake | |
| 8,608,800 B2 | 12/2013 | Portney | |
| 8,613,766 B2 | 12/2013 | Richardson et al. | |
| 8,647,384 B2 | 2/2014 | Lu | |
| 8,657,878 B2 | 2/2014 | Mentak et al. | |
| 8,668,734 B2 | 3/2014 | Hildebrand et al. | |
| 8,690,942 B2 | 3/2014 | Hildebrand et al. | |
| 8,715,345 B2 | 5/2014 | DeBoer et al. | |
| 8,715,346 B2 | 5/2014 | De Juan, Jr. et al. | |
| 8,734,509 B2 | 5/2014 | Mentak et al. | |
| 8,771,347 B2 | 7/2014 | DeBoer et al. | |
| 8,814,934 B2 | 8/2014 | Geraghty et al. | |
| 8,834,565 B2 | 9/2014 | Nun | |
| 8,858,626 B2 | 10/2014 | Noy | |
| 8,867,141 B2 | 10/2014 | Pugh et al. | |

(56) References Cited

U.S. PATENT DOCUMENTS

| | | | |
|---|---|---|---|
| 8,900,298 B2 * | 12/2014 | Anvar | A61F 2/1613 623/6.13 |
| 8,900,300 B1 | 12/2014 | Wortz | |
| 8,956,408 B2 | 2/2015 | Smiley et al. | |
| 8,968,396 B2 | 3/2015 | Matthews et al. | |
| 8,968,399 B2 | 3/2015 | Ghabra | |
| 8,992,609 B2 | 3/2015 | Shadduck | |
| 9,005,282 B2 | 4/2015 | Chang et al. | |
| 9,005,283 B2 | 4/2015 | Nguyen et al. | |
| 9,034,035 B2 | 5/2015 | Betser et al. | |
| 9,044,317 B2 | 6/2015 | Hildebrand et al. | |
| 9,072,600 B2 | 7/2015 | Tran | |
| 9,090,033 B2 | 7/2015 | Carson et al. | |
| 9,095,424 B2 | 8/2015 | Kahook et al. | |
| 9,125,736 B2 | 9/2015 | Kahook et al. | |
| 9,186,244 B2 | 11/2015 | Silvestrini et al. | |
| 9,198,752 B2 | 12/2015 | Woods | |
| 9,277,987 B2 | 3/2016 | Smiley et al. | |
| 9,289,287 B2 | 3/2016 | Kahook et al. | |
| 9,326,846 B2 | 5/2016 | Devita Gerardi et al. | |
| 9,333,072 B2 | 5/2016 | Ichikawa | |
| 9,358,103 B1 | 6/2016 | Wortz et al. | |
| 9,364,316 B1 | 6/2016 | Kahook et al. | |
| 9,387,069 B2 | 7/2016 | Kahook et al. | |
| 9,421,088 B1 | 8/2016 | Kahook et al. | |
| 9,427,312 B2 | 8/2016 | DeBoer et al. | |
| 9,433,497 B2 | 9/2016 | DeBoer et al. | |
| 9,456,895 B2 | 10/2016 | Shadduck | |
| 9,486,311 B2 | 11/2016 | Argento et al. | |
| 9,610,155 B2 | 4/2017 | Matthews | |
| 9,622,852 B2 | 4/2017 | Simonov et al. | |
| 9,629,712 B2 | 4/2017 | Stenger | |
| 9,636,213 B2 | 5/2017 | Brady | |
| 9,655,716 B2 | 5/2017 | Cumming | |
| 9,681,946 B2 | 6/2017 | Kahook et al. | |
| 9,693,858 B2 | 7/2017 | Hildebrand et al. | |
| 9,713,526 B2 | 7/2017 | Rombach | |
| 9,713,527 B2 | 7/2017 | Nishi et al. | |
| 9,717,589 B2 | 8/2017 | Simonov et al. | |
| 9,744,027 B2 | 8/2017 | Jansen | |
| 9,744,028 B2 | 8/2017 | Simonov et al. | |
| 9,795,473 B2 | 10/2017 | Smiley et al. | |
| 9,808,339 B2 | 11/2017 | Dorronsoro Diaz et al. | |
| 9,814,568 B2 | 11/2017 | Ben Nun | |
| 9,814,570 B2 | 11/2017 | Robert et al. | |
| 9,820,849 B2 | 11/2017 | Jansen | |
| 9,848,980 B2 | 12/2017 | McCafferty | |
| 9,855,137 B2 | 1/2018 | Smiley et al. | |
| 9,855,139 B2 | 1/2018 | Matthews et al. | |
| 9,861,469 B2 | 1/2018 | Simonov et al. | |
| 9,872,762 B2 | 1/2018 | Scholl et al. | |
| 9,872,763 B2 | 1/2018 | Smiley et al. | |
| 9,877,825 B2 | 1/2018 | Kahook et al. | |
| 9,883,940 B2 | 2/2018 | Nishi et al. | |
| 9,925,039 B2 | 3/2018 | Sohn et al. | |
| 9,925,040 B2 | 3/2018 | Kahook et al. | |
| 9,931,202 B2 | 4/2018 | Borja et al. | |
| 9,987,126 B2 | 6/2018 | Borja et al. | |
| 10,004,596 B2 | 6/2018 | Brady et al. | |
| 10,028,824 B2 | 7/2018 | Kahook et al. | |
| 10,045,844 B2 | 8/2018 | Smiley et al. | |
| 10,080,648 B2 | 9/2018 | Kahook et al. | |
| 10,111,745 B2 | 10/2018 | Silvestrini et al. | |
| 10,159,564 B2 | 12/2018 | Brady et al. | |
| 10,195,018 B2 | 2/2019 | Salahieh et al. | |
| 10,195,020 B2 | 2/2019 | Matthews | |
| 2002/0005344 A1 * | 1/2002 | Heidlas | C08G 77/36 203/49 |
| 2002/0055776 A1 | 5/2002 | Juan, Jr. et al. | |
| 2002/0071856 A1 | 6/2002 | Dillingham et al. | |
| 2002/0120329 A1 | 8/2002 | Lang et al. | |
| 2003/0093149 A1 | 5/2003 | Glazier | |
| 2003/0105522 A1 | 6/2003 | Glazier | |
| 2003/0109926 A1 | 6/2003 | Portney | |
| 2003/0158295 A1 | 8/2003 | Fukuda et al. | |
| 2004/0082993 A1 * | 4/2004 | Woods | A61F 2/1635 623/6.28 |
| 2004/0082994 A1 | 4/2004 | Woods et al. | |
| 2004/0111152 A1 | 6/2004 | Kelman | |
| 2004/0148023 A1 | 7/2004 | Shu | |
| 2004/0162612 A1 | 8/2004 | Portney et al. | |
| 2004/0169816 A1 | 9/2004 | Esch | |
| 2004/0249455 A1 | 12/2004 | Tran | |
| 2005/0021139 A1 | 1/2005 | Shadduck | |
| 2005/0071002 A1 | 3/2005 | Glazier | |
| 2005/0107873 A1 | 5/2005 | Zhou | |
| 2005/0137703 A1 | 6/2005 | Chen | |
| 2005/0251253 A1 | 11/2005 | Gross | |
| 2005/0251254 A1 | 11/2005 | Brady et al. | |
| 2005/0267575 A1 | 12/2005 | Nguyen et al. | |
| 2006/0041307 A1 | 2/2006 | Esch et al. | |
| 2006/0047339 A1 | 3/2006 | Brown | |
| 2006/0069178 A1 | 3/2006 | Rastogi et al. | |
| 2006/0074487 A1 | 4/2006 | Gilg | |
| 2006/0111776 A1 | 5/2006 | Glick et al. | |
| 2006/0134173 A1 | 6/2006 | Liu et al. | |
| 2006/0135477 A1 | 6/2006 | Haitjema et al. | |
| 2006/0212116 A1 | 9/2006 | Woods | |
| 2006/0238702 A1 | 10/2006 | Glick et al. | |
| 2006/0241752 A1 | 10/2006 | Israel | |
| 2007/0016293 A1 | 1/2007 | Tran | |
| 2007/0032868 A1 | 2/2007 | Woods | |
| 2007/0050024 A1 | 3/2007 | Zhang | |
| 2007/0050025 A1 | 3/2007 | Nguyen et al. | |
| 2007/0078515 A1 | 4/2007 | Brady et al. | |
| 2007/0088433 A1 | 4/2007 | Esch et al. | |
| 2007/0100445 A1 | 5/2007 | Shadduck | |
| 2007/0106377 A1 | 5/2007 | Smith et al. | |
| 2007/0118216 A1 | 5/2007 | Pynson | |
| 2007/0129798 A1 | 6/2007 | Chawdhary | |
| 2007/0129799 A1 | 6/2007 | Schedler | |
| 2007/0129800 A1 | 6/2007 | Cumming | |
| 2007/0129801 A1 | 6/2007 | Cumming | |
| 2007/0132949 A1 | 6/2007 | Phelan | |
| 2007/0213817 A1 | 9/2007 | Esch et al. | |
| 2007/0260308 A1 | 11/2007 | Tran | |
| 2007/0260310 A1 | 11/2007 | Richardson | |
| 2008/0015689 A1 | 1/2008 | Esch et al. | |
| 2008/0033547 A1 | 2/2008 | Chang et al. | |
| 2008/0046074 A1 | 2/2008 | Smith et al. | |
| 2008/0046075 A1 | 2/2008 | Esch et al. | |
| 2008/0046077 A1 | 2/2008 | Cumming | |
| 2008/0051886 A1 | 2/2008 | Lin | |
| 2008/0154364 A1 | 6/2008 | Richardson et al. | |
| 2008/0200982 A1 * | 8/2008 | Your | A61L 27/16 623/6.37 |
| 2008/0269887 A1 | 10/2008 | Cumming | |
| 2008/0300680 A1 | 12/2008 | Nun | |
| 2008/0306587 A1 * | 12/2008 | Your | A61L 27/16 623/6.11 |
| 2008/0306588 A1 | 12/2008 | Smiley et al. | |
| 2008/0306589 A1 | 12/2008 | Donitzky et al. | |
| 2009/0005865 A1 | 1/2009 | Smiley et al. | |
| 2009/0027661 A1 | 1/2009 | Choi et al. | |
| 2009/0043384 A1 | 2/2009 | Niwa et al. | |
| 2009/0125106 A1 | 5/2009 | Weinschenk, III et al. | |
| 2009/0149952 A1 | 6/2009 | Shadduck | |
| 2009/0198326 A1 | 8/2009 | Zhou et al. | |
| 2009/0204209 A1 | 8/2009 | Tran | |
| 2009/0204210 A1 | 8/2009 | Pynson | |
| 2009/0264998 A1 | 10/2009 | Mentak et al. | |
| 2009/0292355 A1 | 11/2009 | Boyd et al. | |
| 2009/0319040 A1 | 12/2009 | Khoury | |
| 2010/0004742 A1 | 1/2010 | Cumming | |
| 2010/0055449 A1 | 3/2010 | Ota | |
| 2010/0057095 A1 | 3/2010 | Khuray et al. | |
| 2010/0094412 A1 | 4/2010 | Wensrich | |
| 2010/0094413 A1 | 4/2010 | Rombach et al. | |
| 2010/0131058 A1 | 5/2010 | Shadduck | |
| 2010/0179653 A1 | 7/2010 | Argento et al. | |
| 2010/0204787 A1 | 8/2010 | Noy | |
| 2010/0211169 A1 | 8/2010 | Stanley et al. | |
| 2010/0228344 A1 | 9/2010 | Shadduck | |
| 2010/0288346 A1 | 9/2010 | Esch | |

(56) References Cited

U.S. PATENT DOCUMENTS

| | | |
|---|---|---|
| 2010/0324672 A1 | 12/2010 | Esch et al. |
| 2010/0324674 A1 | 12/2010 | Brown |
| 2011/0029074 A1 | 2/2011 | Reisin et al. |
| 2011/0071628 A1 | 3/2011 | Gross et al. |
| 2011/0118834 A1 | 5/2011 | Lo et al. |
| 2011/0118836 A1 | 5/2011 | Jain |
| 2011/0224788 A1 | 9/2011 | Webb |
| 2011/0282442 A1 | 11/2011 | Scholl et al. |
| 2011/0288638 A1 | 11/2011 | Smiley et al. |
| 2012/0016473 A1 | 1/2012 | Brady et al. |
| 2012/0035724 A1 | 2/2012 | Clarke |
| 2012/0071972 A1 | 3/2012 | Zhao |
| 2012/0078364 A1 | 3/2012 | Stenger |
| 2012/0095125 A1* | 4/2012 | Hu ............ A61K 8/895 523/105 |
| 2012/0232649 A1 | 9/2012 | Cuevas |
| 2012/0245683 A1 | 9/2012 | Christie et al. |
| 2012/0253458 A1 | 10/2012 | Geraghty et al. |
| 2012/0253459 A1 | 10/2012 | Reich et al. |
| 2012/0290084 A1 | 11/2012 | Coroneo |
| 2012/0296423 A1 | 11/2012 | Caffey |
| 2012/0296424 A1 | 11/2012 | Betser |
| 2012/0310341 A1 | 12/2012 | Simonov et al. |
| 2012/0310343 A1 | 12/2012 | Van Noy |
| 2013/0006353 A1 | 1/2013 | Betser et al. |
| 2013/0035760 A1 | 2/2013 | Portney |
| 2013/0038944 A1 | 2/2013 | Chang et al. |
| 2013/0060331 A1 | 3/2013 | Shadduck |
| 2013/0110234 A1 | 5/2013 | DeVita et al. |
| 2013/0110235 A1 | 5/2013 | Shweigerling |
| 2013/0116781 A1 | 5/2013 | Nun |
| 2013/0131794 A1 | 5/2013 | Smiley et al. |
| 2013/0190867 A1 | 7/2013 | Peyman |
| 2013/0231741 A1 | 9/2013 | Clarke |
| 2013/0250239 A1 | 9/2013 | Hildebrand et al. |
| 2013/0268070 A1 | 10/2013 | Esch et al. |
| 2013/0297018 A1 | 11/2013 | Brady et al. |
| 2013/0317607 A1 | 11/2013 | DeBoer et al. |
| 2013/0317608 A1 | 11/2013 | Hermans et al. |
| 2014/0012277 A1 | 1/2014 | Matthews et al. |
| 2014/0058507 A1 | 2/2014 | Reich et al. |
| 2014/0085726 A1 | 3/2014 | Portney |
| 2014/0100654 A1 | 4/2014 | Portney et al. |
| 2014/0107459 A1 | 4/2014 | Lind et al. |
| 2014/0111765 A1 | 4/2014 | DeBoer et al. |
| 2014/0121768 A1 | 5/2014 | Simpson |
| 2014/0135917 A1 | 5/2014 | Glazier |
| 2014/0135918 A1 | 5/2014 | De Juan, Jr. et al. |
| 2014/0172092 A1 | 6/2014 | Carson et al. |
| 2014/0180404 A1 | 6/2014 | Tram |
| 2014/0180405 A1 | 6/2014 | Weinschenk, III et al. |
| 2014/0180406 A1 | 6/2014 | Simpson |
| 2014/0180407 A1 | 6/2014 | Sohn et al. |
| 2014/0180410 A1 | 6/2014 | Gerardi |
| 2014/0227437 A1 | 8/2014 | DeBoer et al. |
| 2014/0228949 A1 | 8/2014 | Argento et al. |
| 2014/0249625 A1 | 9/2014 | Shadduck |
| 2014/0257478 A1 | 9/2014 | McCafferty |
| 2014/0257479 A1 | 9/2014 | McCafferty |
| 2014/0309734 A1 | 10/2014 | Sohn et al. |
| 2015/0087743 A1 | 3/2015 | Anvar et al. |
| 2015/0105760 A1 | 4/2015 | Lensgen |
| 2015/0127102 A1 | 5/2015 | Wortz |
| 2015/0173892 A1 | 6/2015 | Borja et al. |
| 2015/0202041 A1 | 7/2015 | Shadduck |
| 2015/0216652 A1 | 8/2015 | Jansen |
| 2015/0238310 A1 | 8/2015 | Matthews et al. |
| 2015/0366656 A1 | 12/2015 | Wortz et al. |
| 2016/0000558 A1 | 1/2016 | Honigsbaum |
| 2016/0008126 A1 | 1/2016 | Salahieh et al. |
| 2016/0051361 A1 | 2/2016 | Phillips |
| 2016/0058553 A1* | 3/2016 | Salahieh ............ A61F 2/1629 623/6.13 |
| 2016/0074154 A1 | 3/2016 | Woods |
| 2016/0184089 A1 | 6/2016 | Dudee et al. |
| 2016/0184092 A1 | 6/2016 | Smiley et al. |
| 2016/0208138 A1 | 7/2016 | Nishijima et al. |
| 2016/0256265 A1 | 9/2016 | Borja et al. |
| 2016/0262875 A1 | 9/2016 | Smith et al. |
| 2016/0281019 A1 | 9/2016 | Deklippel et al. |
| 2016/0287380 A1* | 10/2016 | Shi ............ A61F 2/1601 |
| 2016/0317287 A1* | 11/2016 | Silvestrini ............ A61F 2/1635 |
| 2017/0020662 A1 | 1/2017 | Shadduck |
| 2017/0049561 A1 | 2/2017 | Smiley et al. |
| 2017/0049562 A1 | 2/2017 | Argento et al. |
| 2017/0216021 A1 | 8/2017 | Brady |
| 2017/0247525 A1 | 8/2017 | Silverstrini et al. |
| 2017/0290658 A1 | 10/2017 | Hildebrand et al. |
| 2017/0319332 A1 | 11/2017 | Kahook et al. |
| 2017/0348095 A1 | 12/2017 | Wortz et al. |
| 2018/0014928 A1 | 1/2018 | Kahook et al. |
| 2018/0028308 A1 | 2/2018 | Smiley et al. |
| 2018/0110613 A1 | 4/2018 | Wortz et al. |
| 2018/0125640 A1 | 5/2018 | Smiley et al. |
| 2018/0132997 A1 | 5/2018 | Smiley et al. |
| 2018/0147051 A1 | 5/2018 | Scholl et al. |
| 2018/0153682 A1 | 6/2018 | Hajela et al. |
| 2018/0161152 A1 | 6/2018 | Argento et al. |
| 2018/0161153 A1 | 6/2018 | Kahook et al. |
| 2018/0177589 A1 | 6/2018 | Argento et al. |
| 2018/0177639 A1 | 6/2018 | Rao et al. |
| 2018/0256315 A1 | 9/2018 | Hildebrand et al. |
| 2018/0271642 A1 | 9/2018 | Wortz et al. |
| 2018/0271645 A1 | 9/2018 | Brady et al. |
| 2018/0280135 A1 | 10/2018 | Otts |
| 2018/0296323 A1 | 10/2018 | Olcina Portilla |
| 2018/0307061 A1 | 10/2018 | State et al. |
| 2018/0318068 A1 | 11/2018 | Otts et al. |
| 2018/0344453 A1 | 12/2018 | Brady |
| 2018/0368971 A1 | 12/2018 | Zacher et al. |
| 2018/0368973 A1 | 12/2018 | Wortz et al. |
| 2018/0368974 A1 | 12/2018 | Kahook et al. |
| 2019/0000612 A1 | 1/2019 | Rao et al. |
| 2019/0015198 A1 | 1/2019 | Kuiper |
| 2019/0021848 A1 | 1/2019 | Kahook et al. |
| 2019/0069989 A1 | 3/2019 | Otts et al. |
| 2019/0076239 A1 | 3/2019 | Wortz et al. |
| 2019/0076243 A1 | 3/2019 | Hadba et al. |
| 2019/0083235 A1 | 3/2019 | Wortz |
| 2019/0099263 A1 | 4/2019 | Brady et al. |

FOREIGN PATENT DOCUMENTS

| | | | |
|---|---|---|---|
| JP | 09150002 A * | 6/1997 | ............ B01D 11/00 |
| JP | H09-150002 A | 6/1997 | |
| WO | WO 92/17132 | 10/1992 | |
| WO | WO 99/29266 | 6/1999 | |
| WO | WO 2001/034067 | 5/2001 | |
| WO | WO 2004/037127 | 5/2004 | |
| WO | WO 2004/052242 | 6/2004 | |
| WO | WO 2004/054471 | 7/2004 | |
| WO | WO 2004/072689 | 8/2004 | |
| WO | WO 2006/047383 | 5/2006 | |
| WO | WO 2007/005778 | 1/2007 | |
| WO | WO 2007/047529 | 4/2007 | |
| WO | WO 2007/047530 | 4/2007 | |
| WO | WO 2008/024766 | 2/2008 | |
| WO | WO 2008/031231 | 3/2008 | |
| WO | WO 2008/077040 | 6/2008 | |
| WO | WO 2008/082957 | 7/2008 | |
| WO | WO 2008/103798 | 8/2008 | |
| WO | WO 2009/015161 | 1/2009 | |
| WO | WO 2009/015226 | 1/2009 | |
| WO | WO 2009/015234 | 1/2009 | |
| WO | WO 2009/015240 | 1/2009 | |
| WO | WO 2010/010565 | 1/2010 | |
| WO | WO 2010/081093 | 7/2010 | |
| WO | WO 2011/026068 | 3/2011 | |
| WO | WO 2011/106435 | 9/2011 | |
| WO | WO 2011/137191 | 11/2011 | |
| WO | WO 2012/006616 | 1/2012 | |
| WO | WO 2012/129407 | 9/2012 | |
| WO | WO 2013/016804 | 2/2013 | |
| WO | WO 2013/070924 | 5/2013 | |

(56) References Cited

FOREIGN PATENT DOCUMENTS

| WO | WO 2013/142323 | 9/2013 |
| WO | WO 2013/166068 | 11/2013 |
| WO | WO 2013/180254 | 12/2013 |
| WO | WO 2013/190130 | 12/2013 |
| WO | WO 2014/099630 | 6/2014 |
| WO | WO 2014/145562 | 9/2014 |
| WO | WO 2014/152017 | 9/2014 |
| WO | WO 2014/197170 | 12/2014 |
| WO | WO 2015/066502 | 5/2015 |
| WO | WO 2015/066532 | 5/2015 |
| WO | WO 2015/126604 | 8/2015 |
| WO | WO 2016/018932 | 2/2016 |
| WO | WO 2016/033217 | 3/2016 |
| WO | WO 2016/122805 | 8/2016 |
| WO | WO 2016/201351 | 12/2016 |
| WO | WO 2017/079449 | 5/2017 |
| WO | WO 2017/079733 | 5/2017 |
| WO | WO 2017/087358 | 5/2017 |
| WO | WO 2017-096087 | 6/2017 |
| WO | WO 2017/192855 | 11/2017 |
| WO | WO 2018/081595 | 5/2018 |
| WO | WO 2018/119408 | 6/2018 |
| WO | WO 2018/167099 | 9/2018 |
| WO | WO 2018/222579 | 12/2018 |
| WO | WO 2018/227014 | 12/2018 |
| WO | WO 2019/005859 | 1/2019 |
| WO | WO 2019/027845 | 2/2019 |
| WO | WO 2009/064876 | 5/2019 |

OTHER PUBLICATIONS

Machine translation of JP-09150002, translation generated Apr. 2018, 6 pages. (Year: 2018).*
Zhou et al. "Strategies for Supercritical CO2 Fractionation of Polydimethylsiloxane" Journal of Applied Polymer Science, 55, 773-778, 1995. (Year: 1995).*
Nakamura et al. "Analysis and Fractionation of Silicone and Fluorosilicone Oils for Intraocular Use" Investigative Ophthamology & Visual Science, 31(10), 1990, 2059-2069. (Year: 1990).*
Gabel et al. "Silicone oil with high specific gravity for intraocular use" British Journal of Ophthamology 1987, 71, 262-267. (Year: 1987).*
International Search Report and Written Opinion for PCT/US17/34803 dated Aug. 23, 2017 (13 pages).
Ehrmann, et al., "Biomechanical analysis of the accommodative apparatus in primates", Clinical and Experimental Optometry, May 2008, vol. 91, Issue 3, pp. 302-312.
Ehrmann, et al., "Ex Vivo Accommodation Simulator II—Concept and Preliminary Results", Proceedings of SPIE vol. 5314, Ophthalmic Technologies XIV, Jul. 2004, pp. 48-58.
Lane, et al., "Comparison of the biomechanical behavior of foldable intraocular lenses", Journal of Cataract Refract Surg, Nov. 2004, vol. 30, pp. 2397-2402.
National Center for Biotechnology Information. PubChem Substance Database; SID=184590955, https://pubchem.ncbi.nlm.nih.gov/substance/184590955 (accessed Sep. 20, 2017).
Zhang, et al., "Fluidic adaptive lens with high focal length tunability", Applied Physics Letters, May 2003, vol. 82, No. 19, pp. 3171-3172.
Zhang, et al., "Integrated fluidic adaptive zoom lens", Optics Letters, Dec. 2004, vol. 29, No. 24, pp. 2855-2857.

* cited by examiner

LENS OIL HAVING A NARROW MOLECULAR WEIGHT DISTRIBUTION FOR INTRAOCULAR LENS DEVICES

CROSS-REFERENCE TO RELATED APPLICATION

The present application claims priority to U.S. Provisional Patent Application No. 62/342,590, entitled "Lens Oil Having a Narrow Molecular Weight Distribution For Intraocular Lens Devices," filed May 27, 2016, the entire contents of which are incorporated by reference into this application.

FIELD OF THE INVENTION

The invention relates generally to lens oil having a narrow molecular weight distribution, and more particularly to lens oil suitable for use in intraocular lens devices.

BACKGROUND

Surgical procedures on the eye have been on the rise as technological advances permit for sophisticated interventions to address a wide variety of ophthalmic conditions. Patient acceptance has increased over the last twenty years, as such procedures have proven to be generally safe and produce results that significantly improve patient quality of life.

Cataract surgery remains one of the most common surgical procedures, with over 16 million cataract procedures being performed worldwide. It is expected that this number will continue to rise as average life expectancies continue to increase. Cataracts are typically treated by removing the crystalline lens from the eye and implanting an intraocular lens ("IOL") in its place. Conventional IOL devices typically provide vision correction at only a single distance via a monofocal lens, and thus fail to correct for presbyopia. Accordingly, while patients who undergo a standard IOL implantation no longer experience clouding from cataracts, they are unable to accommodate, or change focus from near to far, from far to near, and to distances in between, and still require use of corrective glasses.

Surgeries to correct refractive errors of the eye have also become extremely common, of which LASIK enjoys substantial popularity with over 700,000 procedures being performed per year. Given the high prevalence of refractive errors and the relative safety and effectiveness of this procedure, more and more people are expected to turn to LASIK or other surgical procedures over conventional eyeglasses or contact lenses. Despite the success of LASIK in treating myopia, there remains an unmet need for an effective surgical intervention to correct for presbyopia, which cannot be treated by conventional LASIK procedures.

As nearly every cataract patient also suffers from presbyopia, there is convergence of market demands for the treatment of both these conditions. Various modifications of IOL devices have been introduced to address ophthalmic cataracts and/or presbyopia in patients. For instance, multifocal lenses for IOL devices were introduced to provide vision correction at more than one distance with the goal of obviating the need for additional corrective lenses required with the monofocal lenses. Multifocal lenses generally have areas of varying refractive power to provide vision at multiple distances (e.g., near, intermediate and far). However, one significant disadvantage to multifocal lenses is the possibility of visual distortions, particularly in the form of glare and halos around light sources at night.

Accommodating IOL devices have also been recently introduced for use in cataract surgery. Accommodating IOL devices often feature a monofocal lens configured to move and/or change shape in response to the eye's natural mechanism of accommodation, thereby providing vision correction over a broad range of distances. Such accommodating IOL devices may also feature a haptic system protruding from the central lens. Such haptic systems are typically configured to respond to the contraction and relaxation of the eye's ciliary muscles and ultimately effect changes in the central lens to provide varying diopters of power.

Some IOL devices may also include a fluid therein, where the movement of said fluid may result in an optical power change. However, conventional fluids have been found to lead to undesirable swelling of the bulk polymer material(s) comprising the IOL device (e.g., the lens, the haptic system, etc.). There is therefore a need to develop improved fluids for use in IOL devices that minimize or eliminate the swelling of the bulk polymer material(s) of said devices.

BRIEF SUMMARY

In one embodiment, silicone oil is provided. The silicone oil can have a mean molecular weight average greater than about 20,000 Daltons and can optionally comprise, no more than about 3% to about 4% of the total silicone oil by weight, components having a molecular weight less than about 15,000 Daltons.

In another embodiment, an intraocular lens (IOL) device is provided. The IOL device can comprise an anterior region, a posterior region, a cavity region defined between the anterior and posterior regions, and a fluid disposed in the cavity region. The fluid can comprise a silicone oil having a mean molecular weight average greater than about 20,000 Daltons. Optionally, no more than about 3% to about 4% of the total silicone oil by weight is comprised of components having a molecular weight less than about 15,000 Daltons.

In yet another embodiment, an intraocular lens (IOL) device configured for implantation in a lens capsule of a patient's eye is provided. The IOL device comprises a silicone oil having a mean molecular weight average greater than about 20,000 Daltons. The silicone oil can be purified such that no component thereof has a molecular weight less than about 5,000 Daltons. The IOL device can also comprise a bulk polymeric material, at least a portion of which can be in physical contact with the silicone oil.

Other objects, features and advantages of the described preferred embodiments will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

Preferred and non-limiting embodiments of the invention may be more readily understood by referring to the accompanying drawings in which.

DETAILED DESCRIPTION OF THE PREFERRED EMBODIMENTS

Specific, non-limiting embodiments of the present invention will now be described with reference to the drawings. It should be understood that particular features and aspects of any embodiment disclosed herein may be used and/or combined with particular features and aspects of any other embodiment disclosed herein. It should also be understood that such embodiments are by way of example and are merely illustrative of but a small number of embodiments within the scope of the present invention. Various changes and modifications obvious to one skilled in the art to which the present invention pertains are deemed to be within the spirit, scope and contemplation of the present invention as further defined in the appended claims.

Unless the context requires otherwise, throughout the present specification and claims, the word "comprise" and variations thereof, such as, "comprises" and "comprising" are to be construed in an open, inclusive sense, that is as "including, but not limited to." The use of all examples, illustrations, and/or exemplary language ("e.g.", "such as", etc.) herein does not impose a limitation on the scope of the invention unless otherwise specified. Furthermore, recitation of numeric ranges of values throughout the specification is intended to serve as a shorthand notation of referring individually to each separate value falling within the range inclusive of the values defining the range, and each separate value is incorporated in the specification as it were individually recited herein. Additionally, the singular forms "a", "an" and "the" include plural referents unless the context clearly dictates otherwise.

Implanted Intraocular Lens Device

Figure 1A:
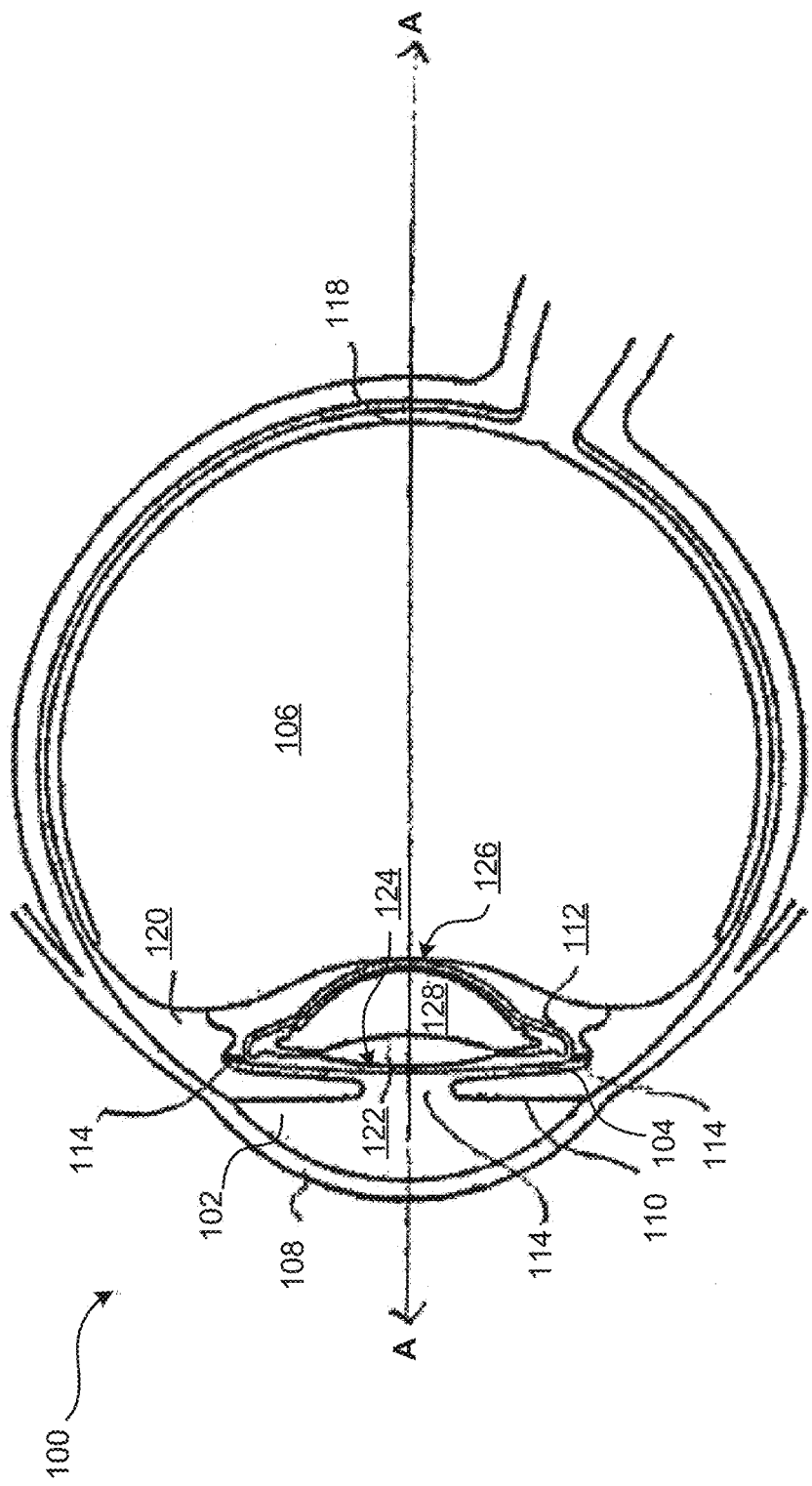
FIGS. 1A and 1B are sectional views illustrating certain anatomical features of the human eye with an intraocular lens (IOL) device implanted in the lens capsule thereof, where the IOL device is in an accommodated and unaccommodated state, respectively.
Figure 1B:
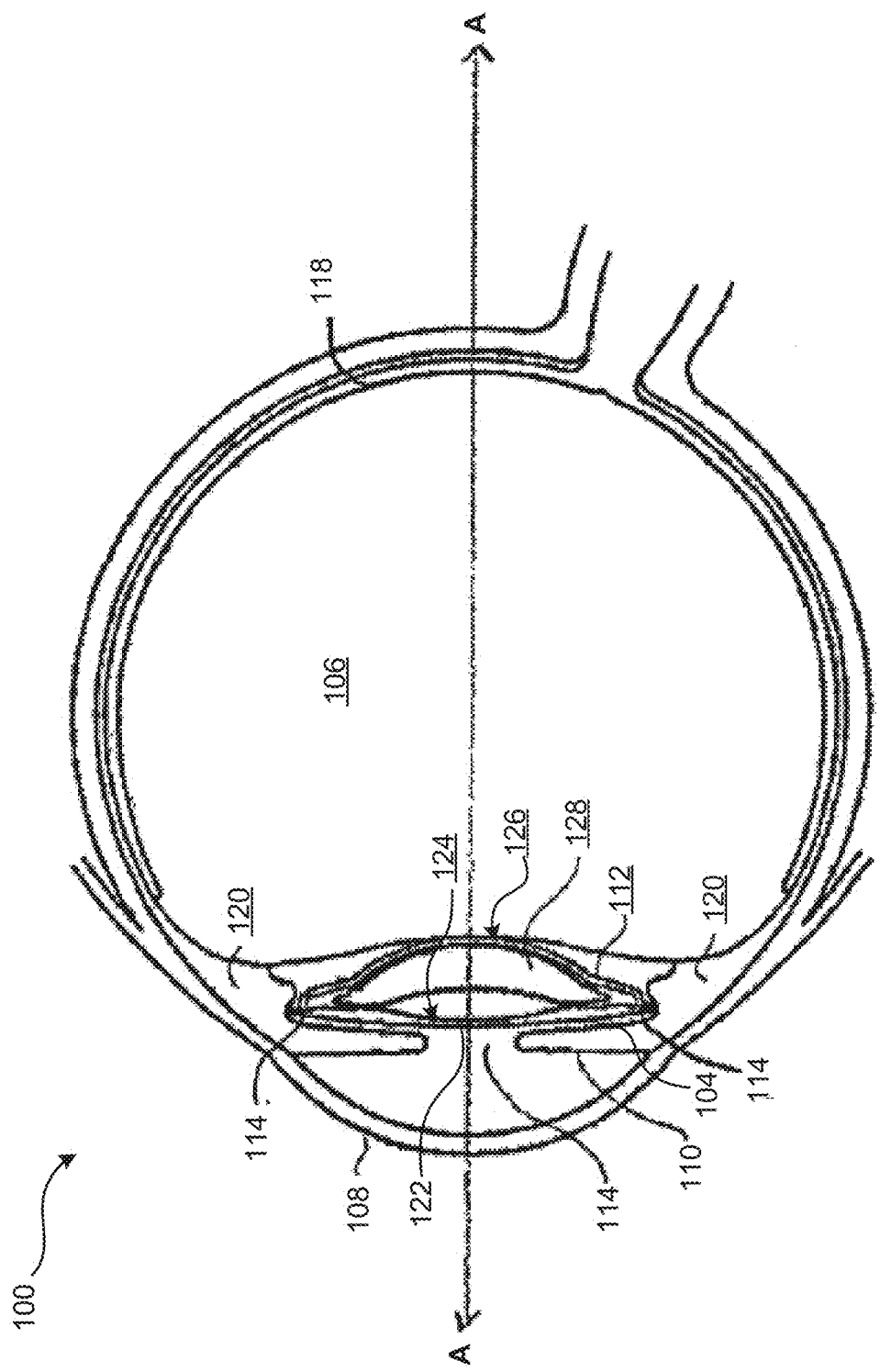

FIGS. 1A-1B illustrate a simplified schematic of a human eye, and a intraocular lens (IOL) device implanted in the lens capsule thereof. As shown in FIGS. 1A-1B, the human eye 100 comprises three fluid-filled chambers: the anterior chamber 102, the posterior chamber 104, and the vitreous chamber 106. The anterior chamber 102 generally corresponds to the region between the cornea 108 and the iris 110, whereas the posterior chamber 104 generally corresponds to the region bounded by the iris 110, the lens capsule 112, and the zonule fibers 114 connected to the lens capsule 112. The anterior and posterior chambers 102, 104 contain the aqueous humor, a fluid which flows therebetween through the pupil 116 (an opening defined by the iris 110). Light enters the eye 100 through the pupil 116 and travels along the visual axis A-A, ultimately striking the retina 118 to produce vision. The amount of light entering the eye 100 is directly related to the size of the pupil 116, which is regulated by the iris 110.

The vitreous chamber 106 generally corresponds to the region between the lens capsule 112 and the retina 118. The vitreous chamber 106 contains the vitreous fluid, a transparent, colorless, gelatinous mass that is more viscous than the aqueous humor. Although much of the volume of the vitreous humor is water, it also contains cells, salts, sugars, vitrosin, a network of collagen type II fibers with glycosaminoglycan hyaluronic acid, and proteins. Preferably, the vitreous has a viscosity that is two to four times that of pure water, giving it a gelatinous consistency. The vitreous humor may also have a refractive index of 1.336.

The lens capsule 112 typically houses the eye's natural lens (not shown). The natural lens is an elastic, clear, crystalline membrane-like structure maintained under tension via the ciliary muscles 120 and zonule fibers 114. As a result, the natural lens tends to have a rounder configuration, a shape it must assume for the eye 100 to focus at a near distance. Changing the shape of the natural lens alters the focus distance of the eye. Accordingly, the eye's natural mechanism of accommodation is reflected by changes in the shape of said lens.

To correct for ophthalmic cataracts and/or presbyopia, the natural lens housed in the lens capsule 112 may be removed and replaced with an IOL device 122. Implantation of the IOL device 122 may be accomplished by first removing the natural lens housed within the lens capsule 112 through a small incision using standard surgical procedures, such as phago-emulsification. After removal of the natural lens, the IOL device 122 may then be introduced into the lens capsule 112 through the small incision.

As shown in the non-limiting embodiment of FIGS. 1A-1B, the IOL device 122 may be characterized as having an anterior region 124 facing the posterior chamber 104 of the eye 100. The anterior region 124 of the IOL device 122 may include a refractive optical element (not shown) centered about the optical axis A-A. The IOL device 122 may also be characterized as having a posterior region 126 coupled to the anterior region 124, with the posterior region 126 facing the vitreous chamber 106 of the eye 100. The IOL device 122 may additionally have a cavity region 128 defined between the anterior and posterior regions 124, 126, in which a fluid (e.g., a lens oil) may be disposed. In some aspects, the fluid may be introduced into the cavity region 128 through a self-sealing valve in the IOL device 122 after implantation of the IOL device 122 in the lens capsule 112. The volume of the fluid contained within the IOL device 122 may be tailored according to the size of the lens capsule 112 for each patient, as would be appreciated by skilled artisans upon reading the present disclosure. In preferred aspects, the volume of the fluid in the cavity region 128 may be sufficient so as to permit engagement of a peripheral region 130 of the IOL device 122 with the zonule fibers 114 and ciliary muscles 120.

Similar to the natural lens, the IOL device 122 changes its shape in response to the accommodative mechanisms of the eye 100. For instance, FIG. 1A shows the eye 100 in a generally accommodated state, as may be the case when the eye 100 is focusing on a nearby object. In such an accommodated state, the ciliary muscles 120 contract and move in an anterior direction. The contraction of the ciliary muscles 120 reduces the stress exerted on the zonule fibers 114, which in turn reduces the stress exerted by the zonule fibers 114 on the lens capsule 112. As a result, the IOL device 122 undergoes elastic recovery and may achieve a more rounded, biconvex shape.

FIG. 1B shows the eye 100 in a generally unaccommodated state, as may be the case when the eye 100 is focusing at a distance. In such an unaccommodated state, the ciliary muscles 120 relax, thereby increasing the diameter of its opening and causing the zonule fibers 114 to pull away from the optical axis A-A. This, in turn, causes the zonule fibers 114 to radially pull on the periphery of the lens capsule 112, which causes the IOL device 122 to assume a flatter shape/ geometry as compared to the accommodated state. The flatter shape/geometry of the lens capsule 112, and the IOL device 122 disposed therein, corresponds to a reduction in the ability to bend or refract light entering the pupil 116.

Intraocular Lens Device

Intraocular lens (IOL) devices suitable for implantation in the lens capsule of a patient's eye may include those described in U.S. Pat. No. 9,186,244, issued Nov. 17, 2015; U.S. Patent Application Publication No. 2013/0053954, published on Feb. 28, 2013; U.S. Patent Application Publication No. 2016/0030161, published on Feb. 4, 2014; U.S. patent application Ser. No. 15/144,544, filed on May 2, 2016; U.S. patent application Ser. No. 15/144,568, filed on May 2, 2016; and International Patent Application Publication No. WO 2016/049059, published on Mar. 31, 2016, the disclosures of which are incorporated herein for reference. It is understood that the silicone oil may be incorporated in the IOL devices described in the foregoing patent references. For example, the silicone oil described herein can be used in place of the fluid described in any one of these patent references. However, for illustrative purposes only, a simplified schematic of an implantable IOL device 200 is shown in FIG. 2, according to one embodiment.

The IOL device 200 of FIG. 2 may be implemented in combination with other devices/features/components described herein, such as those described with reference to other embodiments/aspects, and/or figures. Further, the IOL device 200 may be used in various applications and/or in permutations, which may or may not be noted in the illustrative embodiments/aspects described herein. Moreover, in some embodiments/aspects, the IOL device 200 may include more or less features/components than those shown in FIG. 2.

Figure 2:
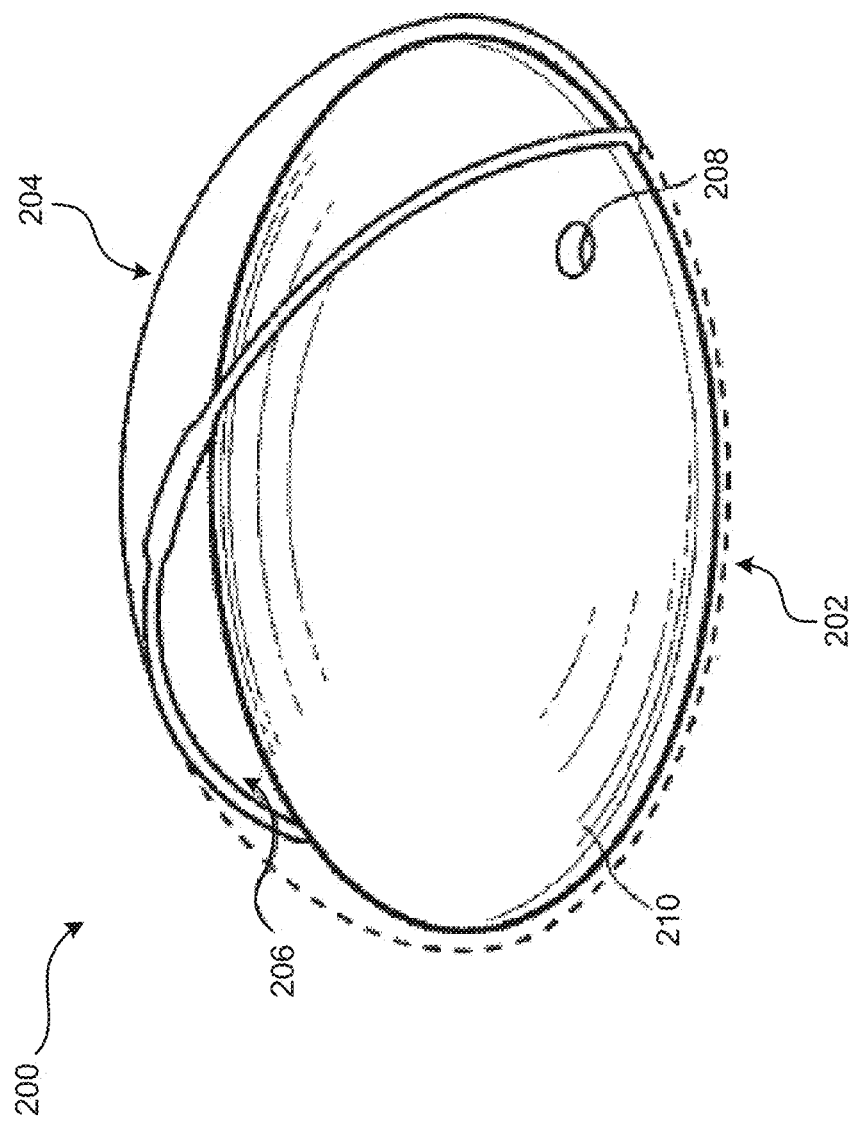
FIG. 2 is a cut-away perspective view illustrating a simplified schematic of an IOL device.

As shown in FIG. 2, the IOL device 200 includes an anterior region 202, and a posterior region 204 coupled to the anterior region 202. The anterior and posterior regions 202, 204 define a cavity region 206, which may be filled with a fluid, e.g., a lens oil. The anterior region 204 may also include an injection port 208 configured to permit injection of the fluid into the cavity region 206. In various aspects, the injection port 208 may include a one-way, self-sealing valve. In other aspects, a separate plug (not shown) may be provided to seal off the injection port 208. While the injection port 208 is shown in FIG. 2 as being located in the anterior region 204 of the IOL device 200, the location of the injection port 208 is not critical, provided the location thereof does not impede vision.

As also shown in FIG. 2, the anterior region 202 of the IOL device includes an optical element 210 that may be optically clear/transparent. Preferably, the optical element 210 may be sufficiently flexible (e.g., has a sufficiently low Young's modulus) so as to respond to the accommodative mechanism of an eye. In particular aspects, the optical element 210 may be sufficiently flexible so as to change its degree of curvature as the ciliary muscles of the eye relax (or contract), thus increasing (or decreasing) the tension of the zonule fibers on the lens capsule of the eye.

In additional aspects, the optical element 210 may be sufficiently flexible so as to change its degree of curvature in response to forces exerted upon the IOL device 200 by the vitreous chamber of the eye. This may be achieved in configurations where the posterior region 204 of the IOL device 200 may be configured to move/actuate in response to the application of an anterior force by the vitreous body during accommodation, thereby causing the fluid disposed in the cavity region 208 to exert a deforming or displacing force on the optical element 210. To effectuate the transfer of the anterior movements of the vitreous chamber upon the lens capsule of the eye, the posterior region 204 of the IOL device 200 preferably comprises a flexible material and contacts a substantial area of the posterior surface of the lens capsule.

In various aspects, the optical element 210 of the IOL device 200 may comprise a first bulk polymer material. This first polymer material may be optically clear/transparent, biocompatible, and flexible (e.g., has a sufficiently low Young's modulus) so as to allow the optical element 210 to change its degree of curvature during accommodation. Suitable materials for the first polymer material may include, but are not limited to, silicone (e.g., alky siloxanes, phenyl siloxanes, fluorinated siloxanes, combinations/copolymers thereof, etc.), acrylic (e.g., alkyl acrylates, fluoracrylates, phenyl acrylate, combinations/copolymers thereof, etc.), plastic, combinations thereof, etc.

As additionally shown in FIG. 2, the posterior region 204 of the IOL device 200 may have an external surface that approximates the posterior surface of an eye's lens capsule, in some aspects. In more aspects, the posterior region 204 of the IOL device 200 may be configured and/or shaped to contact a majority, a substantial, or an entirety of the posterior surface of the eye's lens capsule. In preferred aspects, this point of contact may be at and around the optical axis of the posterior surface of the eye's lens capsule.

In yet further aspects, the posterior region 204 of the IOL device 200 may comprise a second bulk polymer material that may be optically clear/transparent, biocompatible and elastomeric. Suitable materials for the posterior region 204 may include, but are not limited to, silicone (e.g., alky siloxanes, phenyl siloxanes, fluorinated siloxanes, combinations/copolymers thereof, etc.), acrylic (e.g., alkyl acrylates, fluoracrylates, phenyl acrylate, combinations/copolymers thereof, etc.), plastic, combinations thereof, etc. In one particular aspect, the second polymer material of the posterior region 204 may be the same as the first polymer material of the anterior region 202 with regard to one or more of composition, molecular weight, porosity, Young's modulus, hydrophobicity, etc. However, in other aspects, the second polymer material of the posterior region 204 may differ from the first polymer material of the anterior region 202 with regard to one or more of composition, molecular weight, porosity, Young's modulus, hydrophobicity, etc.

While not shown in FIG. 2, the IOL device 200 may optionally include a peripheral region configured to engage the zonule fibers of the eye. This peripheral region may be referred to as a haptic system, and include one or more haptic elements with shapes, configurations, and/or materials as known in the art. In one exemplary aspect, the optional peripheral region(s) may include a third bulk polymer material. The third bulk polymer material of the peripheral region(s) may be the same or different as the first polymer material of the anterior region 202, and/or the same or different as the second polymer material of the posterior region 204, with regard to one or more of composition, molecular weight, porosity, Young's modulus, hydrophobicity, etc.

In yet more aspects, the aforementioned peripheral region may comprise a second cavity region (not shown) in fluidic communication with the cavity region 206 defined by the anterior and posterior regions 202, 204, thereby allowing the fluid (e.g., the lens oil) to flow therebetween. For instance, contraction of the eye's ciliary muscles may deform the peripheral region, driving at least a portion of the fluid in the second cavity region to the cavity region defined by the anterior and posterior regions 202, 204, thereby changing the shape of the optical element 210.

In aspects where the IOL device 200 does not include a peripheral region, the anterior region 202 of the IOL device 200 may have a disk shape of sufficient diameter to engage the zonule fibers of an eye. As would be appreciated by skilled artisans upon reading the present disclosure, the diameter of the anterior region 202 (along with the dimensions associated with any other component of the IOL device 200) may be tailored for each patient according to the particular size requirements of their eye.

Bulk Polymeric Material(s) of IOL Devices

As discussed above, the anterior region, posterior region, and the peripheral region (if present) of an intraocular lens (IOL) device, may each independently include a bulk polymer material. In some embodiments, this bulk polymer material may include, but is not limited to, silicone (e.g., alky siloxanes, phenyl siloxanes, fluorinated siloxanes, combinations/copolymers thereof, etc.), acrylic (e.g., alkyl acrylates, fluoracrylates, phenyl acrylate, combinations/copolymers thereof, etc.), plastic, polymeric hydrogels, and/or other hydrophilic polymer materials suitable for use in an IOL device as would be appreciated by skilled artisans upon reading the present disclosure.

In one illustrative embodiment, a bulk polymer material of the IOL device (e.g. of the anterior region, the posterior region, and/or the peripheral region) may include a fluorosilicone polymer. In some aspects, the fluorosilicone polymer may be a crosslinked copolymer of dialkyl, diphenyl or phenylalkyl siloxane and a fluorinated dialkyl siloxane. The fluorosilicone polymer may be a crosslinked copolymer of dialkyl, diphenyl or phenylalkyl siloxane and trifluoroalkyl (alkyl)siloxane, but may be a terpolymer or higher order polymer of diphenyl and/or phenylalkyl siloxane, dialkyl siloxane and trifluoroalkyl(alkyl)siloxane. In certain aspects, the fluorosilicone polymer may be crosslinked copolymer of dialkyl siloxane, such as dimethyl siloxane, and trifluoroalkyl(alkyl)siloxane, such as 3,3,3-trifluoropropylmethyl siloxane. The ratio of dialkyl siloxane and trifluoroalkyl (alkyl)siloxane may be adjusted to tune the physical properties of the fluorosilicone polymer. For example, increasing the trifluoroalkyl(alkyl)siloxane may increase the hydrophobicity of the resulting fluorosilicone polymer. In various aspects, the fluorosilicone polymer may comprises at least about 25 mole % trifluoroalkyl(alkyl)siloxane, or about 25 mole % trifluoroalkyl(alkyl)siloxane, or about 30 mole % trifluoroalkyl(alkyl)siloxane, or about 35 mole % trifluoroalkyl(alkyl)siloxane, or about 40 mole % trifluoroalkyl (alkyl)siloxane, or about 50 mole % trifluoroalkyl(alkyl) siloxane or from about 25 mole % to about 50 mole %, or from about 25 mole % to about 40 mole % trifluoroalkyl (alkyl)siloxane.

In a specific embodiment, the aforementioned fluorosilicone polymer may be represented by formula (I):

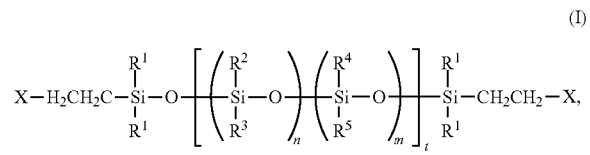

(I)

where n and m are each independently 0 to about 500; t may be about 100 to about 1000; each $R^1$ may be independently alkyl or aryl; $R^2$ may be haloalkyl; $R^3$ may be alkyl or haloalkyl; $R^4$ and $R^5$ are independently alkyl, haloalkyl or aryl; and each X may be a crosslinker that links the polymer of formula (I) with a second polymer of formula (I).

In various aspects, n may be about 50, or about 100, or about 125, or about 150, or about 200, or about 250, or about 300, or about 350, or about 400, or about 450, or about 500. In more aspects, m may be about 50, or about 100, or about 125, or about 150, or about 200, or about 250, or about 300, or about 350, or about 400, or about 450, or about 500. In yet more aspects, n may be about 100, and m may be about 150. In further aspects, t may be about 100, or about 125, or about 150, or about 200, or about 250, or about 300, or about 350, or about 400, or about 450, or about 500, or about 550, or about 600, or about 650, or about 700, or about 750, or about 800, or about 850, or about 900, or about 950, or about 1000.

In additional aspects, each $R^1$ may be alkyl. Suitable alkyl groups include, but are not limited to, $C_1$-$C_6$ alkyl groups such as methyl, ethyl, n-propyl, i-propyl, n-butyl, t-butyl, n-pentyl, n-hexyl, and the like. In some aspects, $R^3$, $R^4$ and $R^5$ are each alkyl, such as defined for $R^1$. In preferred aspects, $R^1$, $R^3$, $R^4$ and $R^5$ are each methyl. In more preferred aspects, $R^2$ may be a haloalkyl group comprising from 1 to 3 halo (provided at least one may be fluoro) substituents. Exemplary haloalkyl groups include, but are not limited to, fluoromethyl, 2-fluorethyl, 2,2-difluoroethyl, and 3,3,3-trifluoropropyl. In one embodiment, $R^2$ may be 3,3,3-trifluoropropyl.

The crosslinker, X, may be a methylhydrosiloxane-dimethylsiloxane copolymer with a methyl-hydrogen content of from about 30 to about 70 mole %, in one aspect. In additional aspects, the crosslinker may have a chain length ranging from about 5 to about 30 repeating Si units (i.e., degree of polymerization).

In still further aspects, a bulk polymeric material of the IOL device may have a degree of polymerization ranging from about 200 to about 500, or from about 300 to about 500, or about 400, or about 450.

In certain embodiments, a bulk polymer material of the IOL device may include a fluorosilicone polymer and up to about 30 wt. % (or about 27 wt. %, or about 25 wt. %, or about 23 wt. %, or about 20 wt. %, or from about 20 to about 30 wt. %) of a silica component. This silica component may have a surface area of at least about 280 $m^2/g$, or at least about 300 $m^2/g$, or at least about 310 $m^2/g$, or at least about 320 $m^2/g$, or at least about 330 $m^2/g$, or at least about 340 $m^2/g$, or at least about 350 $m^2/g$, in some aspects. The silica component may also have an average particle size of less than about 11 nanometers, in more aspects. Fumed silica having an average particle size of about 7 nanometers in diameter may be particularly suitable because the small particle size does not interfere with the wavelength of visible light and contributes to an improved optical resolution in the cured composition. Commercial fumed silica with particle sizes as low as 7 nm are commercially available (e.g., from CABOT and Sigma).

The silica component may be fumed or "activated" silica, which has been treated with a silazane. The amount of silica component should be such that the polymeric material may be sufficiently reinforced, yet remains optically clear. Suitable silazanes and methods for carrying out the fumed silica treatment include the in situ reaction of small particle size fumed silica and are well known in the art. In such reactions, the silazane (e.g., hexamethyldisilazane) readily reacts with the hydroxyl functionalities on fumed silica, forming a trimethylsiloxane coating on the silica surface.

The bulk polymer material of the anterior region, posterior region, and/or the peripheral region (if present) of the IOL devices disclosed herein is not limited to a fluorosilicone polymer, such as a fluorosilicone polymer of Formula I. Rather, the bulk polymer material may include other silicone materials, acrylic materials, plastic materials, and/or other biocompatible and flexible polymer materials suitable for use in an IOL device as would be appreciated by skilled artisans upon reading the present disclosure.

In further embodiments, a bulk polymer material of the IOL device may have a Young's modulus from about 10 psi to about 150 psi, or from about 50 psi to about 100 psi, or about 70 psi. Other physical characteristics of the polymer material can be modulated as well. For instance, the bulk polymer material described herein may have a tensile strength of from about 500 psi to about 1200 psi, or from about 700 psi to about 1000 psi, or about 900 psi, in particular aspects. In more aspects, the bulk polymer material described herein may have a percent elongation of from about 400% to about 1000%, or about 600%.

In one embodiment, the IOL comprises one or a combination of the bulk polymeric material(s) described above in which the silicone oil described herein may be fully encapsulated by the bulk polymeric material(s). In another embodiment, the IOL comprises one or a combination of the bulk polymeric material(s) described above in which the silicone oil described herein may be only partially encapsulated by the bulk polymeric material(s) with the remainder being another material that may be impermeable to the silicone oil.

Lens Oil

One or more of the regions of an IOL device, particularly the bulk polymer material(s) thereof, may be in contact with a fluid, e.g., a lens oil. However, the use of conventional lens oils, such as conventional silicone oils, can result in undesirable swelling of the bulk polymer material(s) associated with IOL devices.

Embodiments disclosed herein are therefore directed to a novel lens oil suitable for use in intraocular lens (IOL) devices. Specifically, the novel lens oil disclosed herein provides for a number of advantages owing to its narrow molecular weight distribution, and the absence/exclusion of low molecular weight components, including the reduction and/or elimination of undesirable swelling of bulk polymeric material associated with IOL devices. In preferred embodiments, the novel lens oil disclosed herein may be a silicone oil.

In one embodiment, the presently disclosed silicone oil may have a mean molecular weight average sufficient to avoid any, or substantially any, swelling of bulk polymeric material associated with the components of IOL devices. For instance, the silicone oil may have a mean molecular weight average of about 20,000 Daltons or greater, according to one aspect. In more aspects, the silicone oil may have a mean molecular weight in a range from about 20,000 Daltons to about 400,000 Daltons.

In particular aspects, the silicone oil may have a mean molecular weight of at least about 20,000 Daltons, at least about 25,000 Daltons, at least about 30,000 Daltons, at least about 35,000 Daltons, at least about 40,000 Daltons, at least about 45,000 Daltons, at least about 50,000 Daltons, at least about 55,000 Daltons, at least about 60,000 Daltons, at least about 65,000 Daltons, at least about 70,000 Daltons, at least about 75,000 Daltons, at least about 80,000 Daltons, at least about 85,000 Daltons, at least about 90,000 Daltons, at least about 95,000 Daltons, at least about 100,000 Daltons, at least about 105,000 Daltons, at least about 110,000 Daltons, at least about 115,000 Daltons, at least about 120,000 Daltons, at least about 125,000 Daltons, at least about 130,000 Daltons, at least about 135,000 Daltons, at least about 140,000 Daltons, at least about 145,000 Daltons, at least about 150,000 Daltons, at least about 155,000 Daltons, at least about 160,000 Daltons, at least about 165,000 Daltons, at least about 170,000 Daltons, at least about 175,000 Daltons, at least about 180,000 Daltons, at least about 185,000 Daltons, at least about 190,000 Daltons, at least about 195,000 Daltons, at least about 200,000 Daltons, at least about 205,000 Daltons, at least about 210,000 Daltons, at least about 215,000 Daltons, at least about 220,000 Daltons, at least about 225,000 Daltons, at least about 230,000 Daltons, at least about 235,000 Daltons, at least about 240,000 Daltons, at least about 245,000 Daltons, at least about 250,000 Daltons, at least about 255,000 Daltons, at least about 260,000 Daltons, at least about 265,000 Daltons, at least about 270,000 Daltons, at least about 275,000 Daltons, at least about 280,000 Daltons, at least about 285,000 Daltons, at least about 290,000 Daltons, at least about 295,000 Daltons, at least about 300,000 Daltons, at least about 305,000 Daltons, at least about 310,000 Daltons, at least about 315,000 Daltons, at least about 320,000 Daltons, at least about 325,000 Daltons, at least about 330,000 Daltons, at least about 335,000 Daltons, at least about 340,000 Daltons, at least about 345,000 Daltons, at least about 350,000 Daltons, at least about 355,000 Daltons, at least about 360,000 Daltons, at least about 365,000 Daltons, at least about 370,000 Daltons, at least about 375,000 Daltons, at least about 380,000 Daltons, at least about 385,000 Daltons, at least about 390,000 Daltons, at least about 395,000 Daltons, or at least about 400,000 Daltons. In another aspect, the silicone oil may have a mean molecular weight within a range that includes any two of the foregoing values.

Additionally, the presently disclosed silicone oil may have a minimal concentration of low molecular weight components to prevent any, or substantially any, swelling of bulk polymeric material associated with IOL devices. In particular aspects, 0% to about 4% of the total silicone oil by weight may be comprised of components having a molecular weight less than about 15,000 Daltons. Stated another way, no more than about 4% of the total silicone oil by weight may be comprised of components having a molecular weight less than about 15,000 Daltons. In preferred aspects, the silicone oil may comprise no more than about 3 wt. %, no more than about 2 wt. %, no more than about 1 wt. %, no more than about 0.05 wt. %, or no more than about 0.005 wt. % of components having a molecular weight less than about 15,000 Daltons.

In more preferred aspects, the total silicone oil by weight may be comprised of components having a molecular weight greater than about 5,000 Daltons. In one non-limiting embodiment, the silicone oil does not include any component having a molecular weight of about 5,000 Daltons or less. The inclusion of components having a molecular weight of about 1,000 Daltons, or about 2,000 Daltons, or about 3,000 Daltons, or about 4,000 Daltons, or even about 5,000 Daltons in the silicone oil may, in certain instances, lead to unfavorable swelling of the bulk polymeric material(s) associated with the IOL devices described herein. In another embodiment, no more than about 3% to about 4% of the total silicone oil by weight may be comprised of components having a molecular weight less than about 15,000 Daltons. In yet another embodiment, no components in the silicone oil have a molecular weight less than 5,000 Daltons.

The presently disclosed silicone oil may further have a narrow molecular weight distribution, and thus a low polydispersity index (PDI), in various embodiments. For example, the silicone oil may have a PDI of about 1.5 or greater, in one exemplary aspect. In another exemplary aspect, the silicone oil may have a PDI of about 2.4.

The presently disclosed silicone oil may have a viscosity in a range from about 4,000 mm²/s at 25° C. to about 100,000 mm²/s at 25° C. in certain embodiments. In preferred aspects, the viscosity of the presently disclosed silicone oil may be about 5,000 mm²/s at 25° C. or greater.

In some aspects, the presently disclosed silicone oil may have a viscosity in a range from about 4,000 mm²/s at 25° C. to about 15,000 mm²/s at 25° C. In exemplary aspects, the silicone oil may have a viscosity of about 4,000 mm²/s at 25° C., about 4,500 mm²/s at 25° C., about 5,000 mm²/s at 25° C., about 5,500 mm²/s at 25° C., about 6,000 mm²/s at 25° C., about 6,500 mm²/s at 25° C., about 7,000 mm²/s at 25° C., about 7,500 mm²/s at 25° C., about 8,000 mm²/s at 25° C., about 8,500 mm²/s at 25° C., about 9,000 mm²/s at 25° C., about 9,500 mm²/s at 25° C., about 10,000 mm²/s at 25° C., about 10,500 mm²/s at 25° C., about 11,000 mm²/s at 25° C., about 11,500 mm²/s at 25° C., about 12,000 mm²/s at 25° C., about 12,500 mm²/s at 25° C., about 13,000 mm²/s at 25° C., about 13,500 mm²/s at 25° C., about 14,000 mm²/s at 25° C., about 14,500 mm²/s at 25° C., or about 15,000 mm²/s at 25° C. The silicone oil may have a viscosity including and between any two of the foregoing values.

In additional aspects, the presently disclosed silicone oil may have a viscosity greater than about 15,000 mm²/s at 25° C. In exemplary aspects, the silicone oil may have a viscosity of about 20,000 mm²/s at 25° C., about 25,000 mm²/s at 25° C., about 30,000 mm²/s at 25° C., about 35,000 mm²/s at 25° C., about 40,000 mm²/s at 25° C., about 45,000 mm²/s at 25° C., about 50,000 mm²/s at 25° C., about 55,000 mm²/s at 25° C., about 60,000 mm²/s at 25° C., about 65,000 mm²/s at 25° C., about 70,000 mm²/s at 25° C., about 75,000 mm²/s at 25° C., about 80,000 mm²/s at 25° C., about 85,000 mm²/s at 25° C., about 90,000 mm²/s at 25° C., about 95,000 mm²/s at 25° C., or about 100,000 mm²/s at 25° C. The silicone oil may have a viscosity including and between any two of the foregoing values.

In additional embodiments, the presently disclosed silicone oil may be substantially index-matched to the bulk material(s) of IOL devices. As used herein, an index-matched material refers to a material whose index of refraction may be about equal to, or closely approximates, the index of refraction of another material. In some aspects, the presently disclosed silicone oil may have an index of refraction in a range from about 1.40 to about 1.60. In particular aspects, the presently disclosed silicone oil may have an index of refraction of about 1.49.

In more embodiments, the presently disclosed silicone oil may comprise an aryl siloxane and an alkyl siloxane. Suitable aryl groups for the aryl siloxane may include, but are not limited to, phenyl, naphthyl, toluyl, xylyl, and the like. Suitable alky groups may include, but are not limited to, methyl, ethyl, n-propyl, i-propyl, n-butyl, t-butyl, n-pentyl, n-hexyl, and the like. The aryl groups of the aryl siloxane may help prevent diffusion of the silicone oil through the bulk polymer material(s) of IOL device due to steric effects. As such, the silicone oil may comprise a greater percentage of aryl siloxane as compared to alky siloxane in some aspects.

In one exemplary embodiment, the silicone oil may comprise a copolymer represented by formula (II):

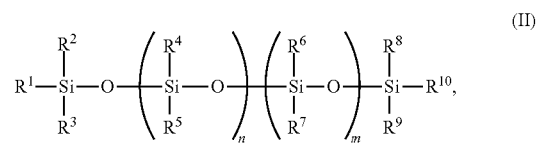

where each of n and m may be independently an integer ranging from 0 to about 500; each $R^1, R^2, R^3, R^4, R^5, R^6, R^7, R^8, R^9$ and $R^{10}$ may be independently hydrogen, alkyl, alkenyl, or aryl, optionally substituted analogs thereof, or other suitable saturated or unsaturated functional group as would be apparent to skilled artisans upon reading the present disclosure.

In various aspects, n may be about 50, or about 100, or about 125, or about 150, or about 200, or about 250, or about 300, or about 350, or about 400, or about 450, or about 500. In more aspects, m may be about 50, or about 100, or about 125, or about 150, or about 200, or about 250, or about 300, or about 350, or about 400, or about 450, or about 500. In some aspects, n and/or m may be integers greater than about 500. The n and m may correspond to integers designated a repeating siloxane unit, where n and m may be independently selected to achieve a desired molecular weight of the resulting silicone copolymer, and/or selected to achieve a desired ratio of the particular siloxane polymer units to which n and m correspond.

As used herein in various aspects, the term "alky" may refer to a straight or branched hydrocarbon chain radical consisting solely of carbon and hydrogen atoms, which may be saturated or unsaturated (i.e., contains one or more double and/or triple bonds), having from one to twenty carbon atoms ($C_1$-$C_{20}$ alkyl), and which may be attached to the rest of the molecule by a single bond. Suitable alkyl groups may include, but are not limited to methyl, ethyl, n-propyl, i-propyl, n-butyl, t-butyl, n-pentyl, n-hexyl, n-heptyl, n-octyl, etc.

As also used herein in various aspects, the term "alkenyl" may refer to a linear or branched hydrocarbon radical having from one to twenty carbon atoms, and containing at least one double bond. Suitable alkenyl groups may include, but are not limited to, vinyl, 2-propenyl, crotyl, 2-isopentenyl, etc.

As further used herein in various aspects, the term "aryl" may refer to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene.

As additionally used herein in various aspects, the term "optionally substituted" may refer to any of the aforementioned functional groups (e.g., alkyl, alkylene, aryl, etc.) where at least one hydrogen atom may be replaced by a bond to a non-hydrogen atoms such as, but not limited to: a halogen atom (e.g., F, Cl, Br, and I); an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Optionally substituted" may also mean any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles.

In some aspects, $R^1$ and/or $R^{10}$ may be hydrogen. In more aspects, each of $R^1$ and $R^{10}$ may be independently alkyl or an optionally substituted alkyl. In yet more aspects, each of $R^1$ and $R^{10}$ may be independently aryl or an optionally substituted analog thereof.

In still more aspects, $R^1$ and/or $R^{10}$ may be independently alkenyl or an optionally substituted alkenyl. In some aspects, $R^1$ and/or $R^{10}$ may be a reactive functional group (e.g., an unsaturated alkenyl) configured to couple (e.g., via a cross-linking reaction) to a reactive group of another polymer, which may also comprise a copolymer of formula (II). Aspects where $R^1$ and/or $R^{10}$ may be a reactive functional group may be especially advantageous for use in an IOL device. For instance, lens oil, e.g., comprising copolymer chains of formula (II) and/or other suitable polymer chains, may be injected into the cavity region of an IOL device via an opening (e.g., valve, port, puncture wound, etc.) in the bulk polymer material thereof, and the opening subsequently sealed via a self-sealing process, a plug, or other suitable means. The inclusion of polymer chains having at least one reactive group (per chain) allows at least some of the polymer chains to be crosslinked with one another, and thereby form a gel, within the IOL device. Moreover, these polymer chains having at least one reactive group (per chain) can participate in the formation of a polymerized sealing plug, and do not interfere with the sealing, by virtue of any residue of the silicone oil becoming crosslinked into the polymer cure of the plug. In some aspects, the silicone oil within the IOL device may be a lightly crosslinked gel, whose unreacted polymer chains do not diffuse through the bulk polymer material of the IOL device.

In one particular aspect, $R^1$ and/or $R^{10}$ may be vinyl. The addition of vinyl terminated reactive silicone copolymers of formula (II) in the cavity region of the IOL device may be beneficial as said copolymers are stable (i.e., do not degrade when exposed to the environment of a human eye), can form a crosslinked gel within the IOL device, and do not interfere, and may participate, with the aforementioned sealing process of the IOL device. As discussed in greater detail below, vinyl terminated reactive silicone polymers of formula (II) may be cured via combination with a suitable crosslinking agent and a curing agent to form the desired, resulting silicone oil, i.e., a silicone oil that does not pass into the free volume of the bulk polymer material of the IOL device and cause swelling thereof.

In one aspect, $R^1$ and/or $R^{10}$ may include a reactive terminal end group other than vinyl in certain aspects. Further, in other aspects, $R^1$ and/or $R^{10}$ may be a non-reactive group (e.g., a saturated functional group) that does not participate in polymerization.

In some aspects, $R^1$ and/or $R^{10}$ may include a methylhydrosiloxane-dimethylsiloxane copolymer with a methyl-hydrogen content ranging from about 30 to about 70 mole %. In particular aspects, the methylhydrosiloxane-dimethylsiloxane copolymer may have chain length of about 5 to about 30 repeating Si units (i.e., degree of polymerization).

In additional aspects, each of $R^2$, $R^3$, $R^8$, and $R^9$ may be independently alkyl, aryl, or optionally substituted analogs thereof. In more aspects, each of $R^2$, $R^3$, $R^8$, and $R^9$ may be independently alkyl or an optionally substituted alkyl. In one such aspect, each of $R^2$, $R^3$, $R^8$, and $R^9$ may be methyl.

In some aspects, each of $R^4$ and $R^5$ may be independently alky, aryl, or optionally substituted analogs thereof. In various aspects, each of $R^4$ and $R^5$ may be independently alkyl or an optionally substituted alkyl. In one such aspect, $R^4$ and/or $R^5$ may be methyl.

In more aspects, each of $R^6$ and $R^7$ may be independently alky, aryl, or substituted analogs thereof. In various aspects, each of $R^6$ and $R^7$ may be independently aryl or an optionally substituted aryl. In one aspect, $R^6$ and/or $R^7$ may be phenyl. In more aspects, $R^6$ may be alkyl and $R^7$ may be aryl. In one such aspect, $R^6$ may be methyl and $R^7$ may be phenyl.

In one exemplary aspect, each of $R^1$ and $R^{10}$ may be vinyl; each of $R^2$, $R^3$, $R^4$, $R^5$, $R^8$, and $R^9$ may be methyl; and each of $R^6$ and $R^7$ may be phenyl. In another exemplary aspect, $R^1$ and $R^{10}$ may be vinyl; each of $R^2$, $R^3$, $R^4$, $R^5$, $R^6$, $R^8$, and $R^9$ may be methyl; and $R^7$ may be phenyl.

In preferred embodiments, the presently disclosed silicone oil may comprise dimethylsiloxane and diphenylsiloxane. Moreover, the silicone oil may comprise dimethylsiloxane in an amount ranging from about 20 mole % to about 25 mole % (preferably about 22 mole % to about 25 mole %), and diphenylsiloxane in an amount ranging from about 80 mole % to about 75 mole % (preferably about 78 mole % to about 75 mole %) in various aspects.

In more embodiments, the presently disclosed silicone oil may comprise dimethylsiloxane (about 0 mole % to about 100 mole %) and methylphenylsiloxane (about 0 mole % to about 100 mole %).

The presently disclosed silicone oil may be manufactured using known synthesis and polymer chemistry techniques. For instance, methods of making the silicone oil may include anionic addition polymerization, living polymerization, living anionic polymerization, etc.

In one non-limiting embodiment, a method of making the presently disclosed silicone oil may comprise: (a) providing vinyl terminated/end-blocked diphenylsiloxane-dimethyl siloxane copolymers to obtain a polymer composition; (b) adding a crosslinking agent and a curing agent to the polymer composition; and (c) curing the polymer composition to obtain a diphenylsiloxane-dimethylsiloxane silicone oil. The vinyl terminated diphenyl siloxane-dimethylsiloxane may be synthesized using known methods from commercially available starting materials or purchased from commercial sources. Suitable vinyl endblockers include, but are not limited to, a vinyl-endblocked dimethyl siloxane oligomer. The resulting oil may also be lightly crosslinked in some aspects, having less than about 5 parts per hundred (pph) crosslinker, or less than about 4 pph, or less than about 2 pph, or less than about 1 pph crosslinker, etc.

In some aspects, the curing step may include addition of a platinum catalyst. The platinum group metal catalyst may be any of the compatible platinum group metal-containing catalysts known to catalyze the addition of silicone-hydrogen atoms to silicon-bonded vinyl radicals. Platinum group metal-containing catalysts may be any of the known forms which are compatible, such as platinic chloride, salts of platinum, chloroplatinic acid and various complexes, for example, silicone complexes with platinum metal-containing groups. The platinum group metal-containing catalyst may be used in any catalytic quantity, such as in an amount sufficient to provide at least about 0.1 ppm weight of platinum group metal (as elemental metal) based on the total weight of the composition. In certain aspects, at least about 10 ppm, or at least about 20 ppm, or at least 30 ppm, or at least about 40 ppm by weight of platinum catalyst may be used.

The presently disclosed silicone oil may be purified using known extraction/fractionation techniques so as to remove low molecular weight components, in preferred embodiments. For example, in one aspect, the silicone oil may be purified via supercritical fluid extraction using supercritical CO2, propane, ethane, ethylene, combinations thereof, and/or other suitable eluting solvent as would be appreciated by skilled artisans upon reading the present disclosure.

In another aspect, size exclusion chromatography (SEC), also referred to as gel permeation chromatography (GPC), may be used to purify the silicone oil. SEC/GPC is a technique that utilizes a column packed with porous cross-linked gels to separate polymer molecules according to their size.

EXAMPLES

An exemplary silicone oil according to the present disclosure was provided, and analyzed as follows.

Figure 3:
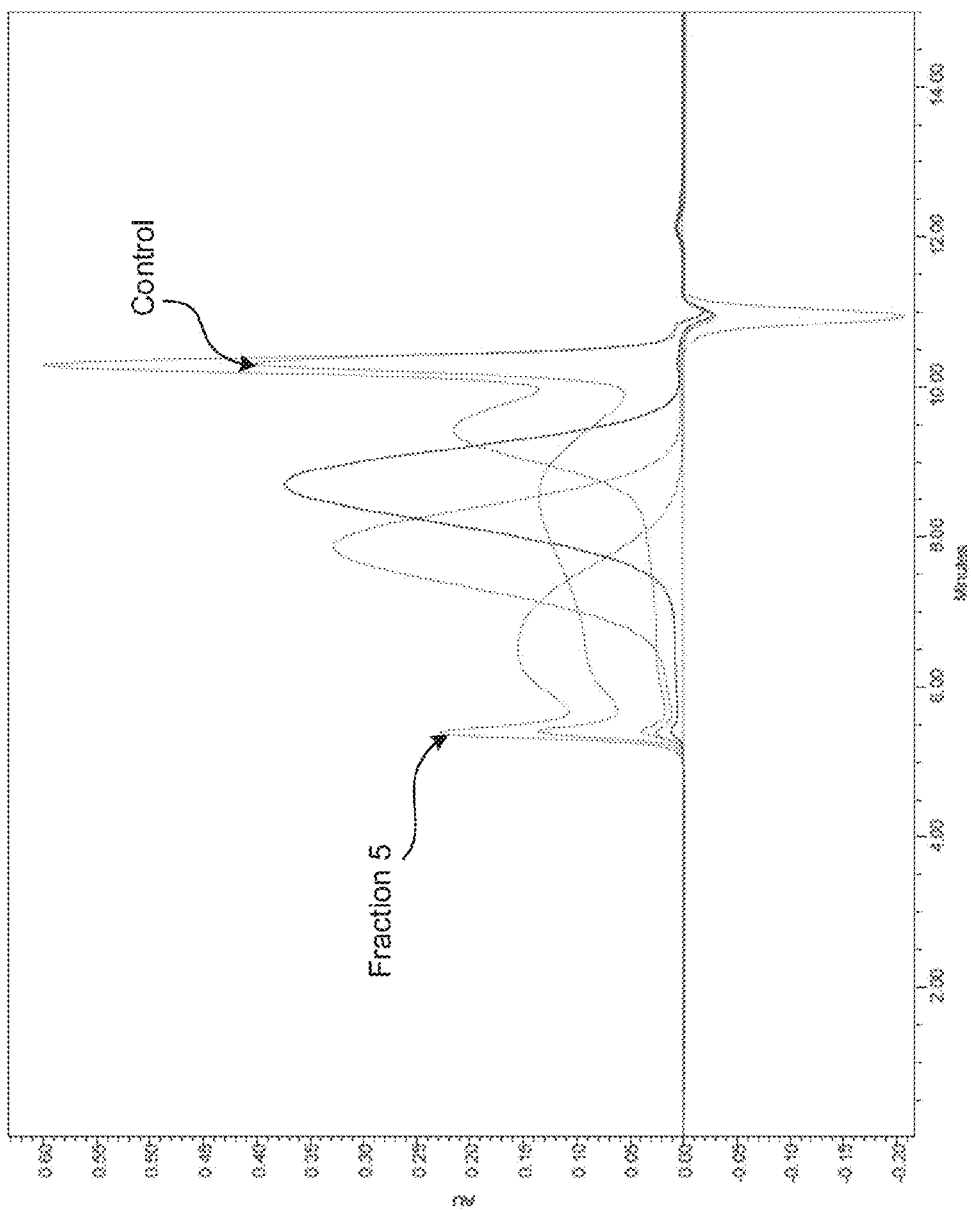
FIG. 3 provides GPC chromatograms for various fractions of diphenyl-dimethyl siloxane obtained via supercritical fluid extraction.

A silicone oil comprised of dimethylsiloxane and diphenysiloxane was fractionated by supercritical fluid extraction. FIG. 3 provides GPC chromatograms of detector response (au) versus retention time (minutes) for various fractions of diphenyl-dimethyl siloxane obtained via supercritical fluid extraction. A UV/VIS detector (256 nm) was used to detect the fractions. Based on a comparison to a GPC calibration curve, fraction 5 indicated in FIG. 3 corresponded to the desired narrow molecular weight distribution, and minimal amount of low molecular weight components disclosed herein (e.g., no more than about 3 wt. % to about 4 wt. % of any component having a molecular weight less than about 15,000 Daltons, and more preferably no components having a molecular weight less than about 5,000 Daltons).

Fraction 5 was further subject to a swell study to determine the degree to which a bulk polymer material of known weight and dimensions swelled when in contact therewith. Such a swell study included preparing a lens (e.g., having a 7 mm shell) comprised of a bulk polymer material, contacting the silicone oil (i.e., fraction 5) to the bulk polymer material, measuring the dimensions and weight of the bulk polymer material over time, and comparing the measurements to the original dimensions and weight of the bulk polymer material. Such comparison provides an indication of how much the polymer material "swelled" (i.e., how much its dimensions and weight increased). It was surprisingly and unexpectedly found that a silicone oil comprised of fraction 5, having less than about 4 wt. % of any component with a molecular weight less than about 15,000 Daltons, and more preferably no components with a molecular weight less than about 5,000 Daltons, resulted in no swelling of the bulk polymer material when in contact therewith. Specifically, the dimensions of the polymer based lens remained at 7 mm after contact with fraction 5.

Figure 4:
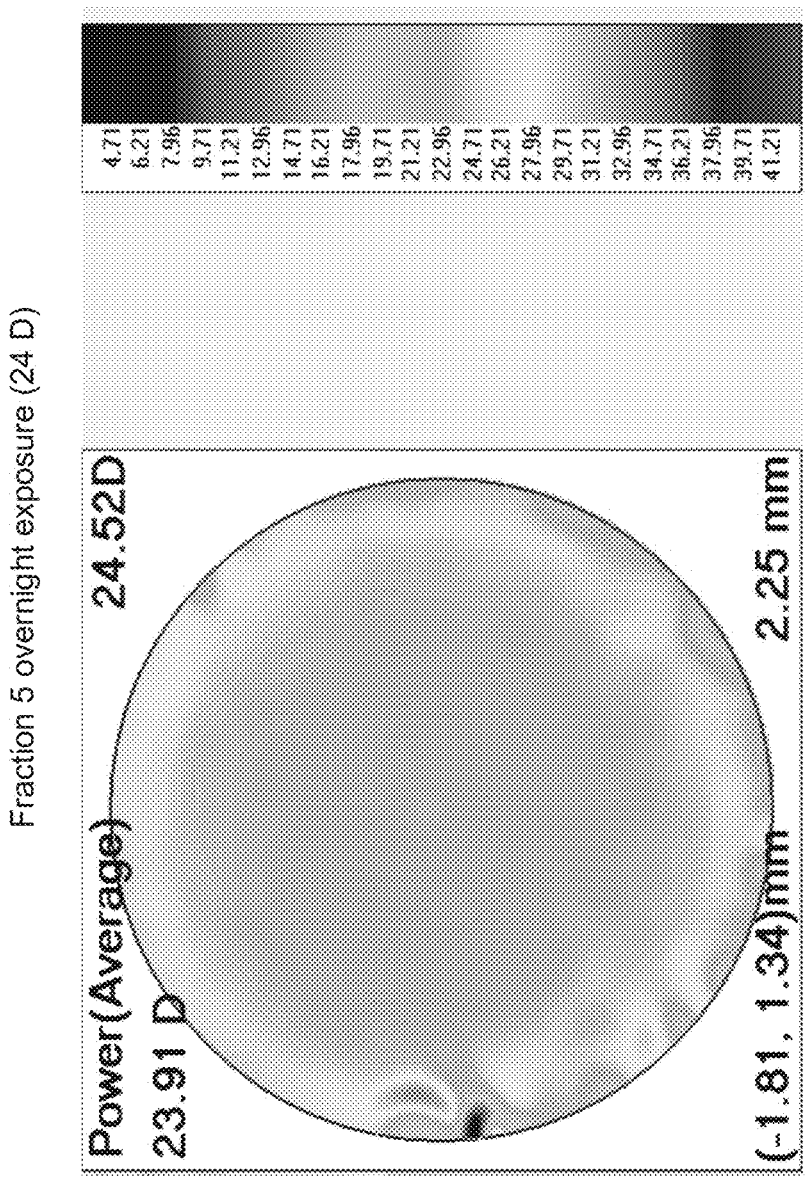
FIG. 4 provides a plot of the measured average power (in diopters) of a polymer based lens after overnight exposure to/contact with an extracted fraction of the diphenyl-dimethyl siloxane described in FIG. 3.

FIG. 4 provides further verification that fraction 5 resulted in no swelling of the polymer lens material to which it was exposed. As indicated above, fraction 5 excludes substantially all low molecular weight components that typically diffuse into the bulk polymer material of an IOL device and which lead to undesirable swelling of the bulk polymer material, as well as undesirable changes in the optical properties of the IOL device. For instance, as shown in FIG. 4, the measurement of the average power (in diopters) of the polymer based lens did not change upon overnight exposure to/contact with fraction 5.

The invention described and claimed herein is not to be limited in scope by the specific preferred embodiments disclosed herein, as these embodiments are intended as illustrations of several aspects of the invention. Indeed, various modifications of the invention in addition to those shown and described herein will become apparent to those skilled in the art from the foregoing description. Such modifications are also intended to fall within the scope of the appended claims.

What is claimed is:

1. A silicone oil having a mean molecular weight in a range from about 20,000 Daltons to about 400,000 Daltons, wherein no more than about 3% to about 4% of the total silicone oil by weight is comprised of components having a molecular weight less than about 15,000 Daltons, the total silicone oil by weight is comprised of components having a molecular weight greater than about 5,000 Daltons, wherein the silicone oil has a viscosity of about 15,000 mm$^2$/s or greater at 25° C., and wherein the silicone oil comprises a co-polymer comprising diphenylsiloxane and dimethylsiloxane.

2. The silicone oil of claim 1, wherein the silicone oil has a viscosity of about 15,000 mm$^2$/s to about 100,000 mm$^2$/s at 25° C.

3. The silicone oil of claim 1, wherein the silicone oil has a refractive index of about 1.49.

4. The silicone oil of claim 1, wherein the silicone oil has a polydispersity index of about 1.5 or greater.

5. The silicone oil of claim 1, wherein the silicone oil comprises about 22 mole % to about 25 mole % diphenylsiloxane and about 78 mole % to about 75 mole % dimethylsiloxane.

6. The silicone oil of claim 1, wherein the silicone oil comprises about 20 mole % to about 25 mole % diphenylsiloxane and about 80 mole % to about 75 mole % of dimethylsiloxane.

7. An intraocular lens (IOL) device, comprising:
an anterior region;
a posterior region;
a cavity region defined between the anterior and posterior regions; and
a fluid disposed in the cavity region, the fluid comprising a silicone oil having a mean molecular weight greater than about 20,000 Daltons, wherein no more than about 3% to about 4% of the total silicone oil by weight is comprised of components having a molecular weight less than about 15,000 Daltons.

8. The IOL device of claim 7, wherein the silicone oil has no component having a molecular weight less than about 5,000 Daltons.

9. The IOL device of claim 7, wherein the silicone oil has a viscosity of about 4,000 mm$^2$/s at 25° C. or greater.

10. The IOL device of claim 7, wherein the silicone oil has a refractive index of about 1.49.

11. The IOL device of claim 7, wherein the silicone oil has a polydispersity index of about 1.5 or greater.

12. The IOL device of claim 7, wherein the silicone oil comprises diphenyl siloxane and dimethylsiloxane.

13. The IOL device of claim 12, wherein the silicone oil comprises about 20 mole % to about 25 mole % of diphenylsiloxane and about 80 mole % to about 75 mole % of dimethylsiloxane.

14. The IOL device of claim 7, wherein the anterior portion comprises a refractive optical element, and wherein at least a portion of the posterior portion comprises an elastic material configured to actuate in response to a force applied thereto, causing the fluid to exert a deforming or displacing force on the refractive optical element.

15. The IOL device of claim 7, wherein at least one of the anterior region and the posterior region comprises a bulk polymeric material.

16. An intraocular (IOL) device configured for implantation in a lens capsule of a patient's eye, the IOL device comprising:

a silicone oil having a mean molecular weight greater than about 20,000 Daltons, wherein the silicone oil is purified such that no component thereof has a molecular weight less than about 5,000 Daltons, and a bulk polymeric material, wherein at least a portion of the bulk material is in physical contact with the silicone oil.

17. The IOL device of claim 16, wherein the silicone oil is entirely encapsulated by the bulk polymeric material.

18. The IOL device of claim 16, wherein the bulk polymeric material is a fluorosilicone polymer may be represented by formula (I):

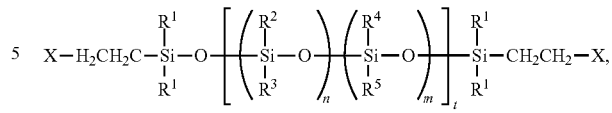

where n and m are each independently 0 to about 500; t is about 100 to about 1000; each $R^1$ is independently alkyl or aryl; $R^2$ is haloalkyl; $R^3$ is alkyl or haloalkyl; $R^4$ and $R^5$ are independently alkyl, haloalkyl or aryl; and each X is a crosslinker that links the polymer of formula (I) with a second polymer of formula (I).

19. The IOL device of claim 18, wherein the crosslinker, X, is a methylhydrosiloxane-dimethylsiloxane copolymer with a methyl-hydrogen content of from about 30 to about 70 mole %.

20. The IOL device of claim 16, wherein the silicone oil is purified using supercritical fluid extraction.

* * * * *

UNITED STATES PATENT AND TRADEMARK OFFICE
CERTIFICATE OF CORRECTION

PATENT NO. : 10,526,353 B2
APPLICATION NO. : 15/607305
DATED : January 7, 2020
INVENTOR(S) : Thomas Silvestrini Page 1 of 1

It is certified that error appears in the above-identified patent and that said Letters Patent is hereby corrected as shown below:

On the Title Page

On page 5, Column 2, (56), Other Publications, Lines 7-8, delete "Ophthamology" and insert -- Ophthalmology --.

On page 5, Column 2, (56), Other Publications, Line 10, delete "Ophthamology" and insert -- Ophthalmology --.

In the Specification

Column 6, Line 16, delete "fluoracrylates," and insert -- fluoroacrylates, --.

Column 6, Line 35, delete "fluoracrylates," and insert -- fluoroacrylates, --.

Column 7, Line 21, delete "fluoracrylates," and insert -- fluoroacrylates, --.

Column 14, Line 45, delete "diphenyl siloxane" and insert -- diphenylsiloxane --.

Column 15, Line 23-24, delete "diphenysiloxane" and insert -- diphenylsiloxane --.

In the Claims

Column 16, Line 59, Claim 12, delete "diphenyl siloxane" and insert -- diphenylsiloxane --.

Signed and Sealed this
Fifteenth Day of September, 2020

Andrei Iancu
*Director of the United States Patent and Trademark Office*